United States Patent
Rowe et al.

(10) Patent No.: US 9,727,699 B2
(45) Date of Patent: Aug. 8, 2017

(54) SOFTWARE TOOL FOR VETERINARIANS

(71) Applicant: TIMELESS VETERINARY SYSTEMS INC., Charlottetown (CA)

(72) Inventors: John L. Rowe, Charlottetown (CA); Brad D. Pineau, Stratford (CA)

(73) Assignee: TIMELESS VETERINARY SYSTEMS INC., Charlottetown, Prince Edward Island (CA)

( * ) Notice: Subject to any disclaimer, the term of this patent is extended or adjusted under 35 U.S.C. 154(b) by 0 days.

(21) Appl. No.: 14/419,470

(22) PCT Filed: Aug. 5, 2013

(86) PCT No.: PCT/CA2013/000692
§ 371 (c)(1),
(2) Date: Feb. 3, 2015

(87) PCT Pub. No.: WO2014/019076
PCT Pub. Date: Feb. 6, 2014

(65) Prior Publication Data
US 2015/0213210 A1   Jul. 30, 2015

Related U.S. Application Data

(60) Provisional application No. 61/679,360, filed on Aug. 3, 2012.

(51) Int. Cl.
*G06F 19/00* (2011.01)
*G06Q 10/10* (2012.01)
*A61B 5/00* (2006.01)

(52) U.S. Cl.
CPC .......... *G06F 19/345* (2013.01); *A61B 5/7264* (2013.01); *A61B 5/7282* (2013.01); *A61B 5/746* (2013.01); *G06Q 10/10* (2013.01)

(58) Field of Classification Search
CPC ..... G06F 19/346; A61B 5/7264; A61B 5/746; G06N 5/02
(Continued)

(56) References Cited

U.S. PATENT DOCUMENTS 6,397,190 B1   5/2002   Goetz
6,482,156 B2   11/2002  Iliff
(Continued)

OTHER PUBLICATIONS

Bellamy, "Medical Diagnosis, Diagnostic Spaces, and Fuzzy Systems", Journal of the American Veterinary Medical Association, vol. 210, No. 3, pp. 390-396, Feb. 1, 1997.
(Continued)

*Primary Examiner* — Paula J Stice
(74) *Attorney, Agent, or Firm* — Norton Rose Fulbright Canada LLP

(57) ABSTRACT

A system and method for generating options for treatment options and pertinent disease information for treating an animal of a first species suffering from an ailment comprises receiving input data representative of a diagnosis of the ailment for the first species, retrieving from a memory at least one treatment protocol associated with the diagnosis as received, and outputting the retrieved at least one treatment protocol. The memory is populated with a plurality of diagnoses each associated with at least a corresponding one of a plurality of treatment protocols adapted for treating at least one animal species and at least one ailment. Each one of the plurality of treatment protocols is supported by evidence-based research.

17 Claims, 47 Drawing Sheets

(58) Field of Classification Search
USPC .......................................................... 600/301
See application file for complete search history.

(56) References Cited

U.S. PATENT DOCUMENTS

| | | | |
|---|---|---|---|
| 7,076,437 B1* | 7/2006 | Levy | G06F 19/322 |
| | | | 600/300 |
| 7,765,114 B2 | 7/2010 | Frick | |
| 7,865,343 B2 | 1/2011 | Dodds | |
| 7,899,687 B2 | 3/2011 | Morris | |
| 2004/0078211 A1 | 4/2004 | Schramm-Apple et al. | |
| 2005/0170323 A1 | 8/2005 | Jarrell et al. | |
| 2007/0244577 A1 | 10/2007 | Jung et al. | |
| 2008/0082358 A1 | 4/2008 | Schmitt et al. | |
| 2009/0078215 A1 | 3/2009 | Lash | |
| 2009/0094060 A1 | 4/2009 | Johnson et al. | |
| 2009/0106044 A1 | 4/2009 | Schweisguth et al. | |
| 2011/0077973 A1 | 3/2011 | Breitenstein et al. | |
| 2011/0246405 A1* | 10/2011 | Dodds | G06F 19/28 |
| | | | 706/46 |
| 2011/0313786 A1 | 12/2011 | Fishman | |

OTHER PUBLICATIONS

Bellamy, "Fuzzy Systems Approach to Diagnosis in the Post-Partum Cow", Journal of the American Veterinary Medical Association, vol. 210, No. 3, pp. 397-401, Feb. 1, 1997.

Carter, "Clinical Decision Support System for Small Animal Practice", Proceedings of the 9th International Symposium on Veterinary Epidemiology and Economics, 2000.

Morris et al., "Decision-Support Tools for Foot and Mouth Disease Control", Rev. Sci. Tech., Off. int. Epiz., vol. 21, No. 3, pp. 557-567, Dec. 2002.

Saegerman et al., "Decision Support Tools for Clinical Diagnosis of Disease in Cows with Suspected Bovine Spongiform Encephalopathy", Journal of Clinical Microbiology, vol. 42, No. 1, pp. 172-178, Jan. 2004.

Sanson, "The Development of a Decision Support System for an Animal Disease Emergency", Thesis, Massey University, 290 pages, 1993.

Alpi et al., "Exploring the State of Veterinary Informatics", The Tenth International Congress on Medical Librarianship, 15 pages, 2009.

\* cited by examiner

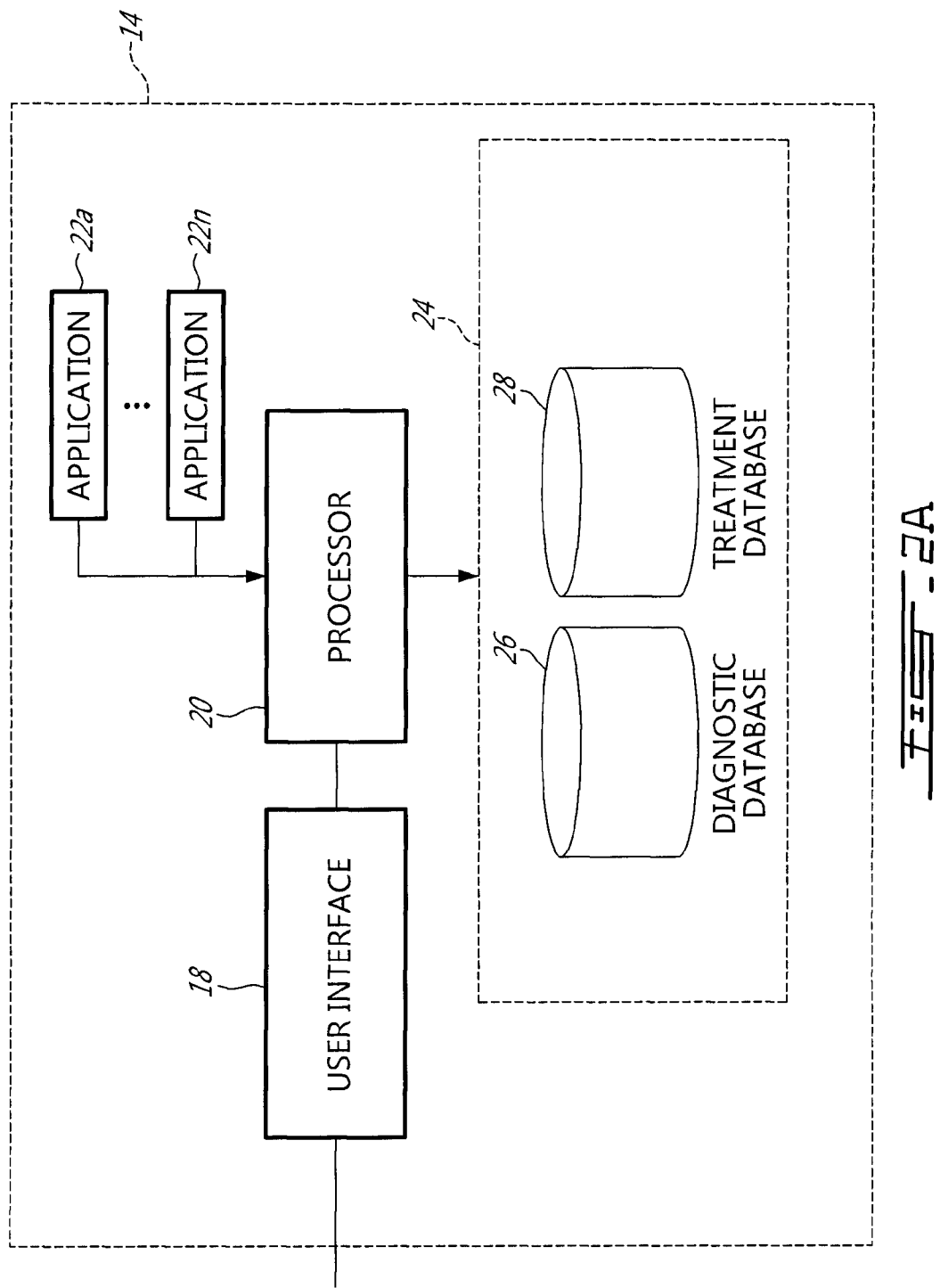

vet_registration
- ⚷ id INT(11)
- ◇ firstName VARCHAR(50)
- ◇ lastName VARCHAR(50)
- ◇ email VARCHAR(255)
- ◇ phone VARCHAR(20)
- ◇ profession VARCHAR(255)
- ◇ institution VARCHAR(255)
- ◇ studentID VARCHAR(20)
- ◇ practiceType VARCHAR(20)
- ◇ city VARCHAR(50)
- ◇ province VARCHAR(50)
- ◇ country VARCHAR(2)
- ◇ howDidYouFindUs TEXT
- ◇ userID INT(11)
- Indexes ▶ vet_country
- ⚷ id INT(11)
- ◇ userID INT(11)
- Indexes ▶ vet_email_queue
- ⚷ id INT(10)
- ◇ dateTimeQueued DATETIME
- ◇ dateTimeSent DATETIME
- ◇ toAddress TEXT
- ◇ ccAddress TEXT
- ◇ bccAddress TEXT
- ◇ fromAddress TEXT
- ◇ replyToAddress TEXT
- ◇ subject VARCHA%R(255)
- ◇ message MEDIUMTEXT
- ◇ isHTML TINYINT(1)
- Indexes ▶ vet_email_template
- ⚷ name VARCHAR(100)
- ◇ subject VARCHAR(255)
- ◇ content TEXT
- ◇ isHTML TINYINT(1)
- ◇ lastEditorID INT(11)
- Indexes ▶ vet_change_log
- ⚷ id INT(11)
- ◇ editorID INT(11)
- ◇ tbl VARCHAR(100)
- ◇ idField VARCHAR(255)
- ◇ idValue VARCHAR(255)
- ◇ col VARCHAR(100)
- ◇ val TEXT
- ◇ replyToAddress TEXT
- ◇ subject VARCHA%R(255)
- ◇ dateTime DATETIME
- ◇ operation VARCHAR(50)
- Indexes ▶

FIG. 2B CONTINUE

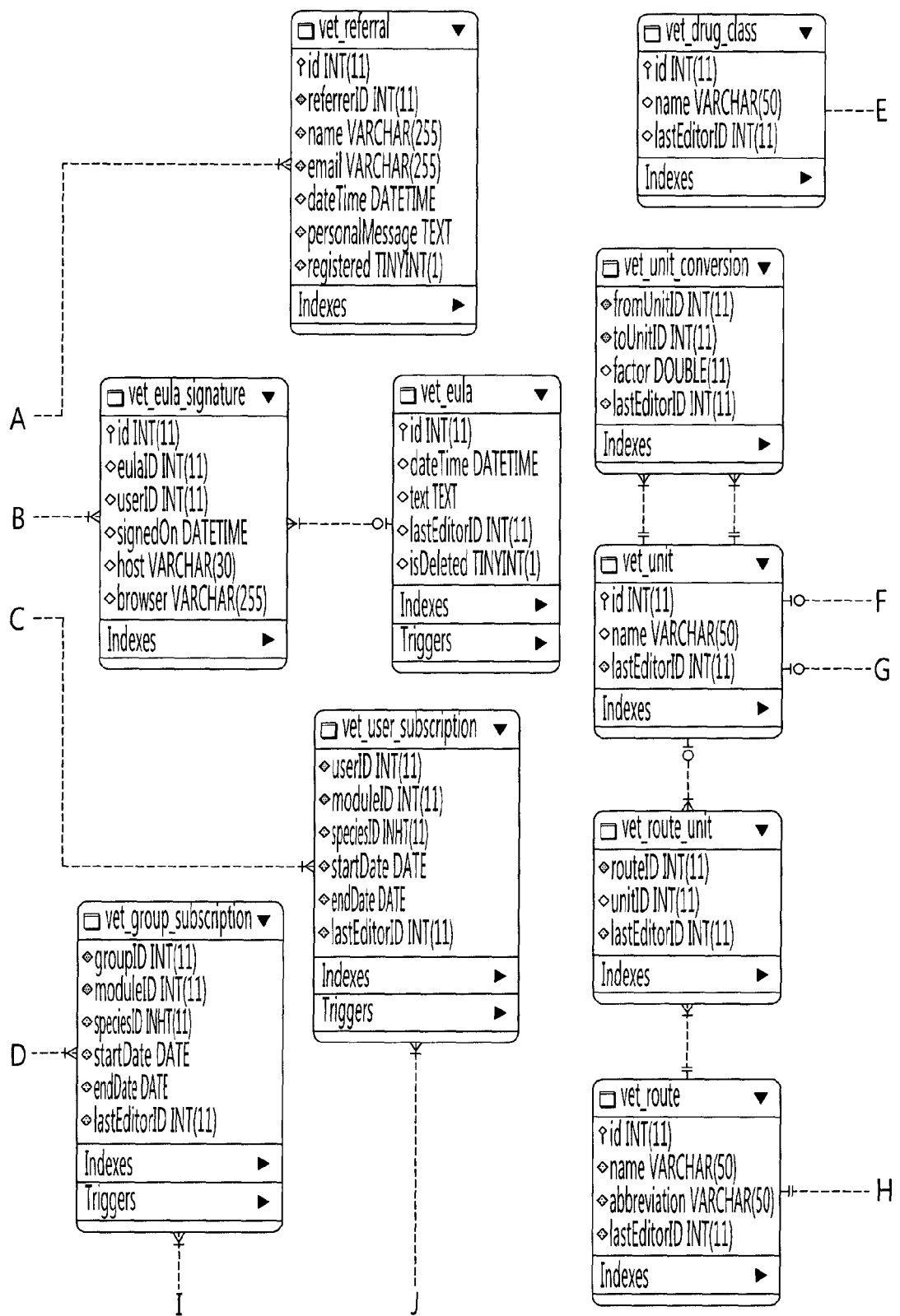
FIG. 2B CONTINUE

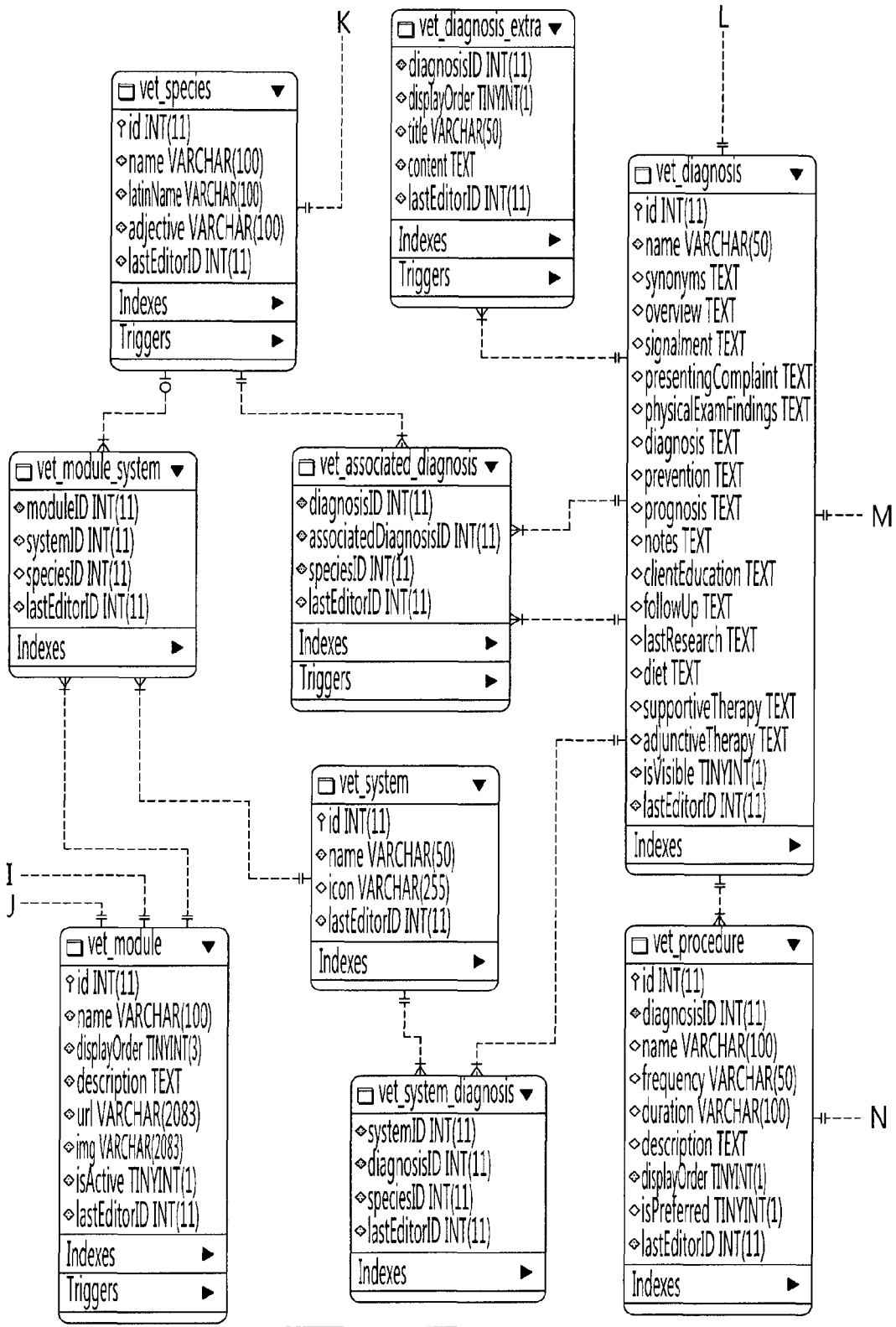
FIG. 2B CONTINUE

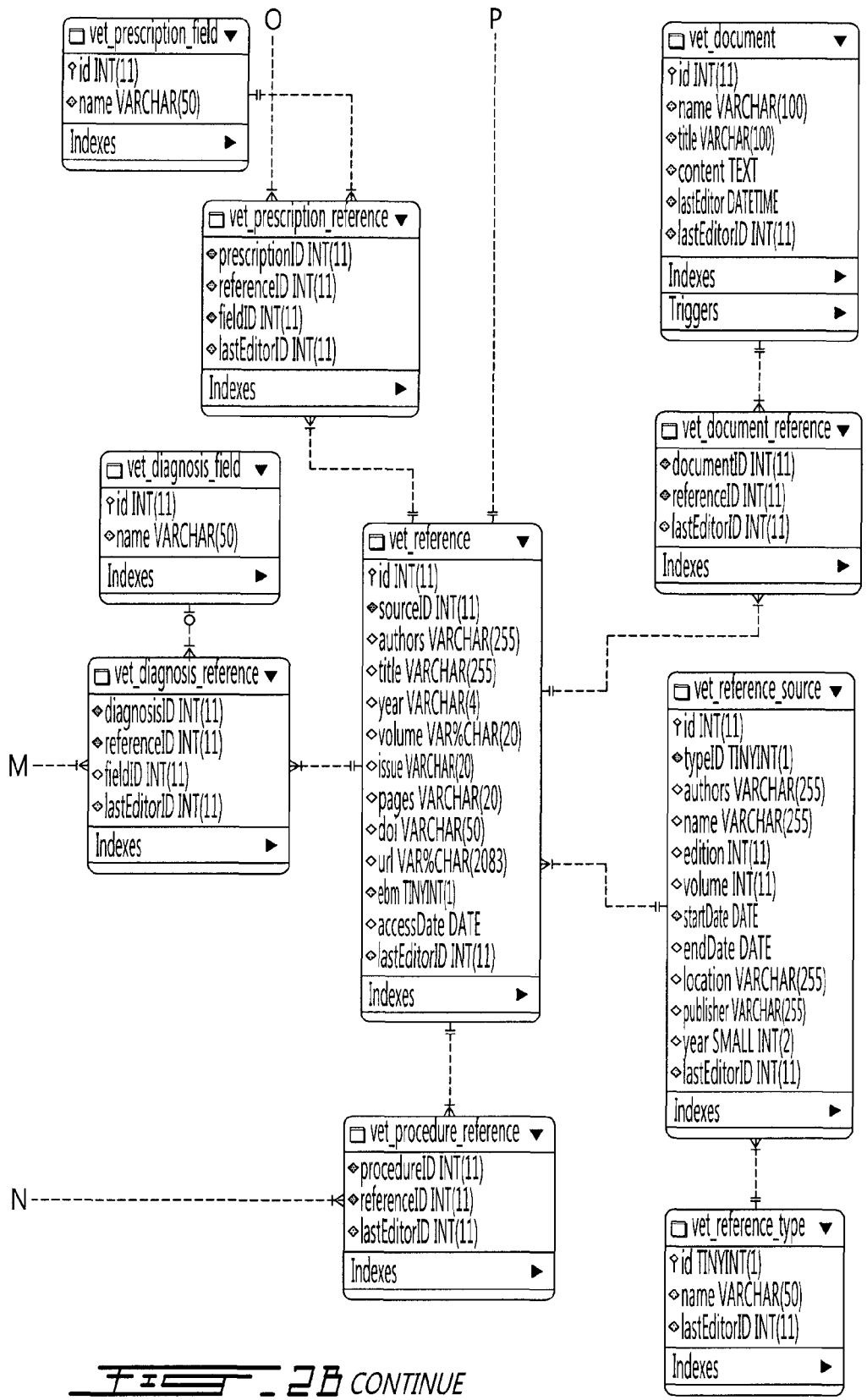
FIG. 2B CONTINUE

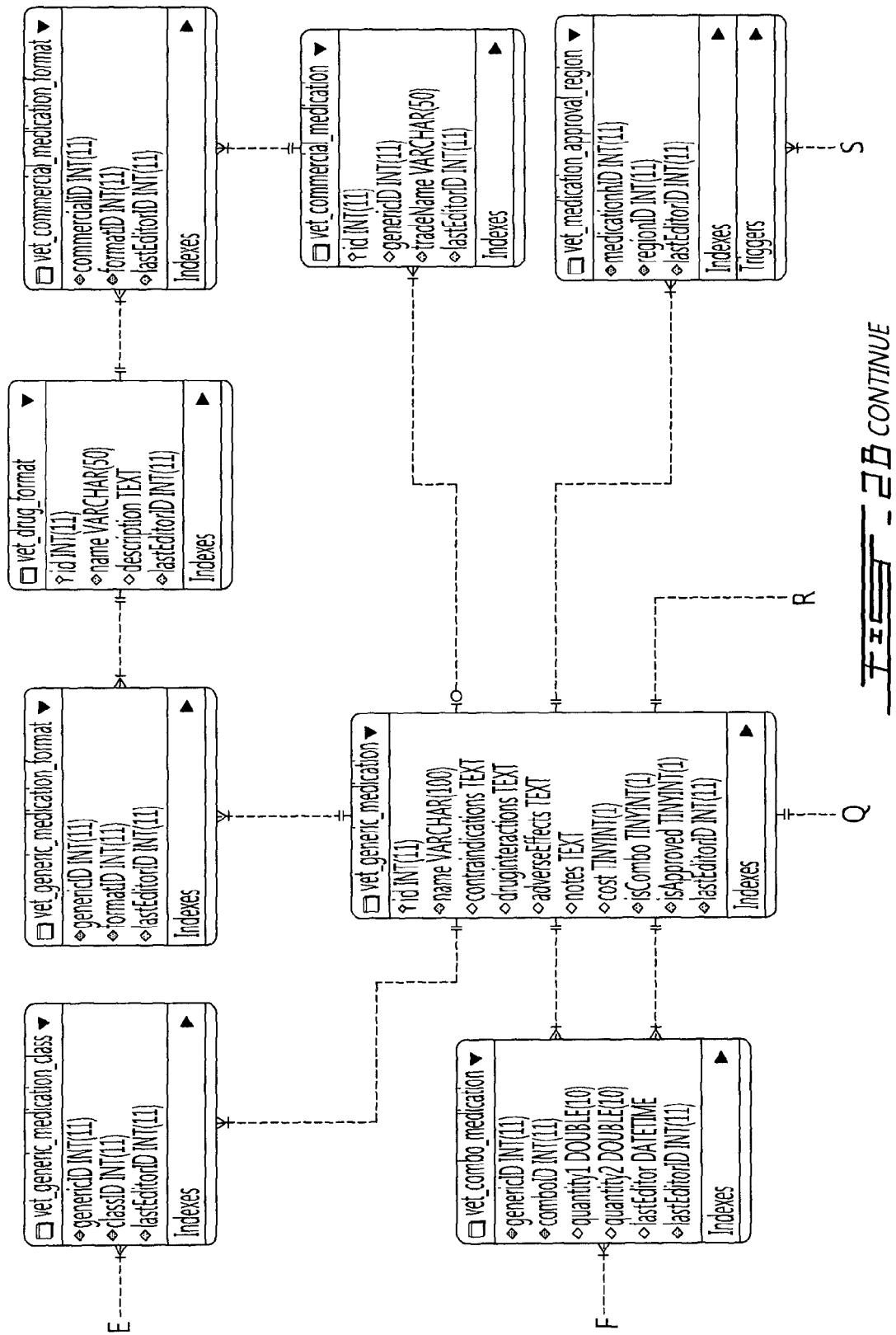
FIG. 2B CONTINUE

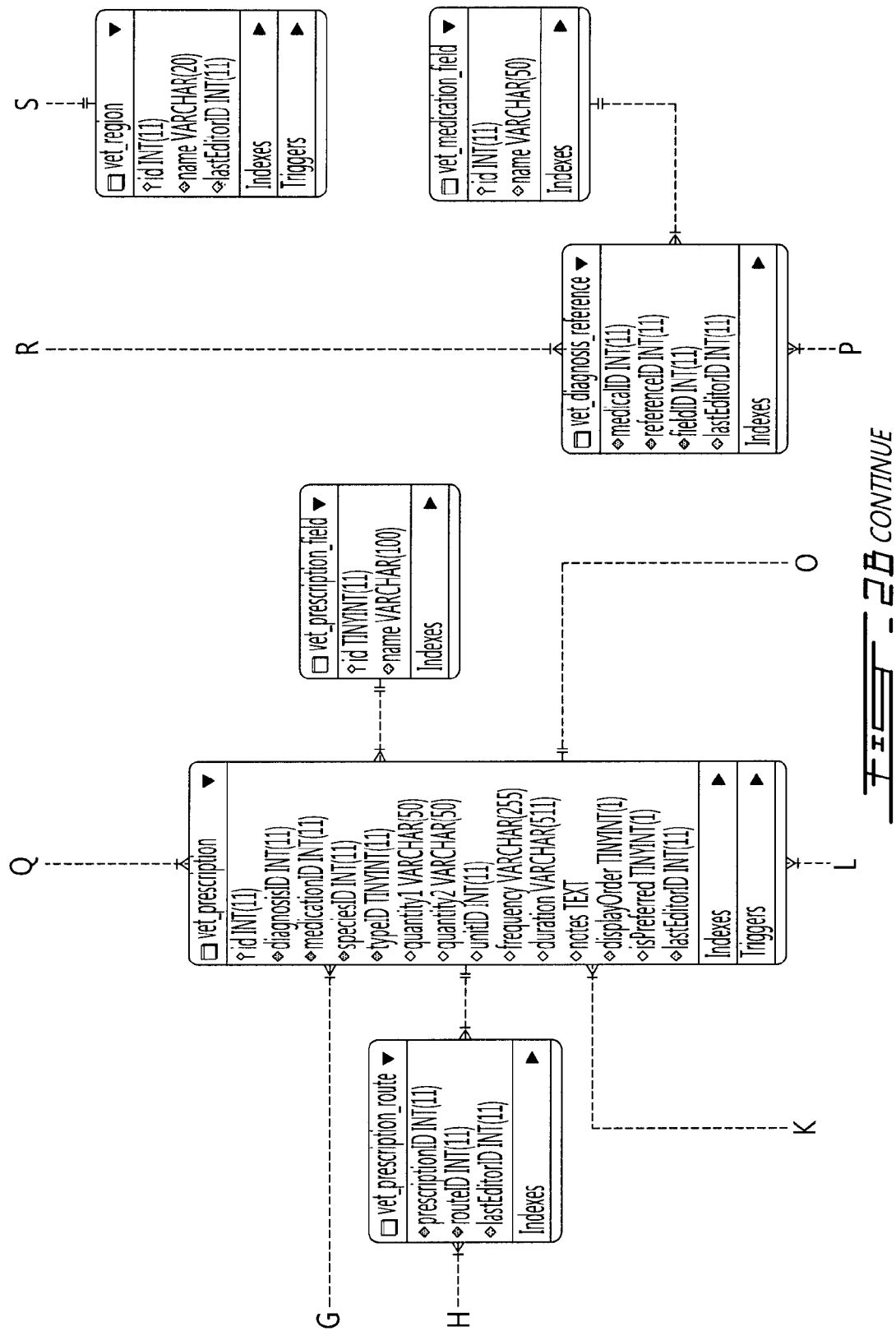
FIG. 2B CONTINUE

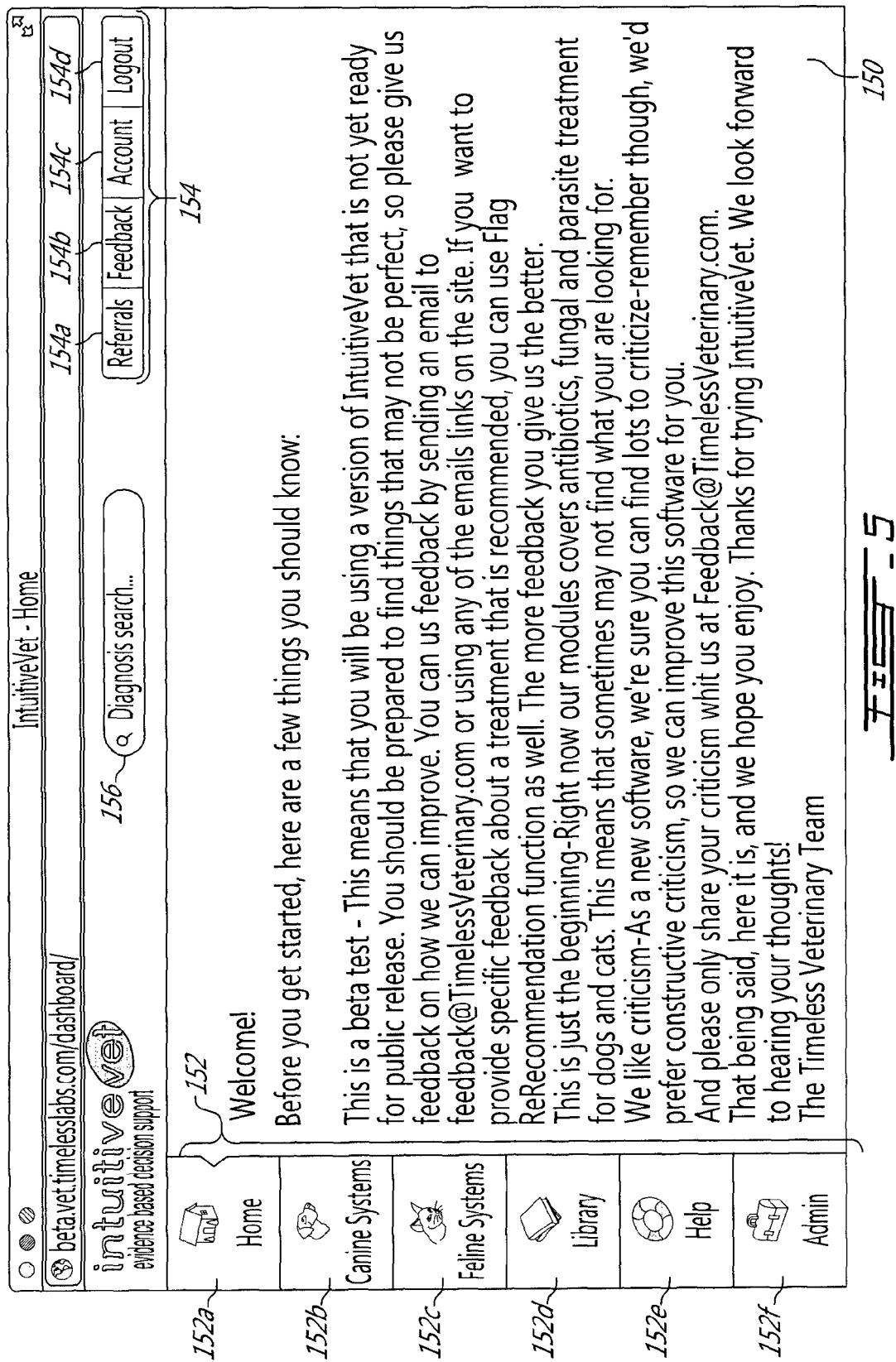

| Polysystemic ▼ | Toxoplasmosis ▼ |

Important notes on Toxoplasmosis

*Toxoplasma gondii* is an enteric coccidian parasite of cats. The enteroepithelial phase is found only in the definitive host the cat. The extraintestinal development of the parasite is similar for all host including dogs, cats, and humans. The tachyzoites of this phase invade and multiply within almost any tissue cell. Parasitemia in pregnancy may result in spread of tachyzoites to the foetus. Degree and severity of illness varies greatly from animal to animal. Clinical toxoplasmosis is most severe in transplacentally infected kittens. Infection of lungs. CNS. and liver are most common sites. No drug can be certain to totally clear the infection.

Dogs can be intermediate hosts. The disease in dogs can be generalized or involve mainly the respiratory, neuromuscular or gastrointestinal system. The generalized disease is more common in dogs less than 1 year of age.

Toxoplasmosis is of public health consideration. Cats shedding oocysts should be treated and hospitalized. especially when pregnant women are in the same vicinity. Dogs do not shed oocysts but they may act as mechanical vectors for the oocysts shed from cats in the same area.

Treatment | Prudent Use

Systemic Treatment Options for Toxoplasmosis

Treatments of choice
[More Info] Clindamycin-3-13 mg/kg (PO, IM) q8h for 4 weeks [1]

Other Treatments
[More Info] Trimethoprim-Sulfa-15 mg/kg (PO) q 12h for 4 weeks [1]
[More Info] Sulfadiazine-30 mg/kg (PO) q 12h for 4 weeks [1]
[More Info] Pyrimethamine-0.25-0.5 mg/kg (PO) q 12h for 4 weeks [1]

Further Reading

1. Dubey JP. Lindsay DS & Lappin MR. *Toxoplasmosis and other intestinal coccidial infections in cats and dogs. Vetrinary Clinics of North america:Small Animal Practice* 2009;39():1009-1034

2. Dubey JP and Lappin MR. *Toxoplasmosis and Neosporosis. In:Greene CE. Infectious Diseases of the dog and cat(2006).3.Philadelphia,USA;WB Saunders,2006;754-775*

FIG. 7A

| Treatment | Comprehensive Treatment | Disease Highlights | Follow-up/Monitoring | Client Education | Latest Research | Associated Diagnoses | Prudent Use |

186
Topical Treatment Options for Perianal Fistula

[More Info] Tacrolimus (0.1%)-applied liberally to affected area (topical) q12h with a gloved hand for 16 weeks and then reduced to the lowest frequency and duration that controls inflammation.* [1,3,4,5,6]

[More Info] Mupirocin-liberally (topical)q12h-24h as needed to reduce bacterial colonization* [2]

188
Systemic Treatment Options for Perianal Fistula

Topical Treatment Options for Perianal Fistula

[More Info] Cyclosporine A-4-8 mg/kg (PO) q12-24h for 8-16 weeks based on clinical improvement. Once significant improvement is noted, the dose can be reduced 20-40% or given q48h.n* [1,2,5,7,8]

[More Info] Cyclosporine A-0.5-5 mg/kg (PO) q12h for 16 weeks* [1,2,5,9,10]

[More Info] Ketoconazole-5-10 mg/kg (PO) q12-24h for 16 weeks* [1,2,5,9,10]

[More Info] Azathioprine-2 mg/kg (PO) q24h for 2-4 weeks (or until a reductionin size, number and severity of fistulas is observed) and then tapered to 1mg/kg q48h and continued 12 weeks as long as myelosuppression does not develop and then tapered to 1mg/kg q48h for a year.* [1,5,11]

[More Info] Prednisone-2-4 mg/kg (PO) q24h for 2-4 weeks and then tapered gradually to the lowest effective dose (<1mg/kg) q48h wich may be required as a lifelong therapy.* [1,2,5,12]

[More Info] Amoxicillin/Clavulanate-12.5-25 mg/kg (PO) q8-12h for at least 2 weeks.* [5,13]

| Treatment | Comprehensive Treatment | Disease Highlights | Follow-up/Monitoring | Client Education | Prudent Use |

Topical Treatment Options for Otitis Externa, Fungal

Treatments of Choice

[More Info] Miconazole-enough to coat the entire lenght of the ear canal otic application (topical) q12h for 10-14d* [3,8]

Commercial Names: Miconazole

Treatment notes
　　　When infection is strictly yeast, miconazole on its own (Conofite lotion) or with a steroid added to it (Synotic) is more appropriate than combination topical therapy.
　　　Adverse Effects
　　　■ Skin irritation possible.
　　　■ User should avoid contact with eyes and wash hands thoroughly after applying or use gloves.

*198* — Flag this treatment

*196*

[More Info] Ketoconazole-Ear cleaner otic application (topical) q12h for 10-14d* [2]

Other Treatments

[More Info] Clotrimazole-enough to coat the entire length of the ear canal otic application (topical) q12h for 10-14d* [3,8]

[More Info] Nystatin-enough to coat the entire length of the ear canal otic application (topical) q12h for 10-14d* [3]

FIG. 7C

[More Info] Thiabendazole-enough to coat the entire length of the ear canal otic application (topical) q12h for 10-14d* [3,8]

[More Info] Silver sulfadiazine-enough to coat the entire length of the ear canal otic application (topical) q12h for 10-14d*

Systemic Treatment Options for Otitis Externa, Fungal

Treatments of Choice
[More Info] Ketoconazole-5-10 mg/kg (PO) q12-24h with food for 1-2 weeks beyond cytological cure* [1,2,6]

Other Treatments
[More Info] Fluconazole-5-10 mg/kg (PO) q12-24h with food for 1-2 weeks beyond cytological cure* [1,6]
[More Info] Itraconazole-5-10 mg/kg (PO) q12-24h with food for 1-2 weeks beyond cytological cure* [1,6]

| Treatment | Comprehensive Treatment | Disease Highlights | Follow-up/Monitoring | Client Education | Prudent Use |

*210*

Diet/Lifestyle — *210a*

As many cases of OE in dogs are due to hypersensitivity reactions, a hypoallergenic diet or elimination diet may be essential for controlling OE secondary to hypersensitivity. This tends to be less important in feline cases of Oe.
[5]

Supportive Therapy — *210b*

To pluck or not to pluck? Plucking of hairs from external ear canal in hairy-eared individuals is controversial. It can incite inflammation which can cause or worse otitis. In cases of hairy-eared dogs with otitis, plucking small amounts of hair frequently may be benefit. Plucking ear hair from dogs without otitis is of questionable benefit and not recommended. This tends not to be an issue in cats.
[9]

Adjunct Therapy — *210c*

Ear cleaning is a very important part of treatment. Initially, this is done to facilitatae examination of the tympanum and may need to be done under sedation or general anesthesia depending on severity. There are many different ear cleaners and these usually contain astringents, detergent, disinfectants, ceruminlytics, and/or antimicrobials/antifungals/anti-inflammatories. Cleaning should be performed prior to starting therapy (typically in the hospital setting) and then by the client on a regular basis (daily to every other day during infection). Over-cleasing can actually lead to ear infctions (secondary to maceration) and thus the client education is important to ensure it is don properly.

Systemic administration of steroids is valuable when there is severe pruritus or inflammation present.
This may in fact be the most useful aspect of therapy, especially when the underlying cause is due to a hypersensitivity. The most commonly used steroid for dogs is prednisone, 1 mg/kg q24h PO for the first 10-14 days of treatment when severe pain/pruritus is present. The most commonly used steroid for cats is prednisolone, 2 mg/kg q24h PO for the first 10-14 days of treatment when severe pain/pruritus is present. Steroids should be gradually tapered before discontinuing.
[1,5,6]

FIG. 6A

| Treatment | Comprehensive Treatment | Disease Highlights | Follow-up/Monitoring | Client Education | Associated Diagnoses | Prudent Use |

*212*

Overview — *212a*

*Bartonella spp.* are gram-negative bacteria that infect erythocytes and have the ability to affect numerous systems in the body. Primarily the cardiovascular system is affected, as in the case of bacterial endocarditis and hematological disturbances caused by Bartonellosis;however, skin(bacillary angiomatosis) and subcuateous tissue, liver (hepatitis, eye(uvetis), respiratory (granulomatous rhinitis, pneumonitis), musculoskeletal (polyarthritis) and neurological systems (meningoradiculoneuritis, meningitis) can also be affected. Thisdisease is typically transmitted though blood-sucking arthropods (fleas and ticks are most commonly implicated). This disease has zoonotic implications and cats represent a large reservoir for human infection. The role that dogs play in human infection is unclear but they appear to serve as excellent sentinels for human exposure. *B. henselae* is the most common species to affect the cat and is the cause of Cat Scratch Disease in people. *B. vinsonii* is the most common species implicated in endocarditis attributable to *Bartonella* in dogs.

[1,2,3,8,9,10,11]

Signalment — *212b*

Prevalence of infection varies depending on climate and infection rates within the population. Warmer climates have significantly higher infection rate than colder climates. Bartenollosis tends to affect cats (young and stray cats are over represented) more so than dogs. However, in cats symptoms can be minimal or non-existant and *Bartonella spp.* are considered stealth pathogens in felines.

[1,2]

History & Presenting Complaint — *212c*

Highly dependant upon the system affected and ranges from nonspecific symptoms of lethargy, anorexia and weight loss to sudden death associated with aortic valve bacterial endocarditis

FIG. 8B

Physical Exam Findings — 212d

Highly dependant upon the system affected but in dogs these could include fever, splenomegaly, lameness, vasculitis, heart murmur, lymphadenopathy, hepatomegaly, uveitis, dermatological lesions, neurological signs, nasal discharge (including epistaxis). Cats tend to to show less clinical signs but may demonstrate fever, uveitis, lymphadenopathy, mild neurological signs and and heart murmurs associated with aortic valve endocarditis.
[3,8]

Diagnostics — 212e

CBC reveals thrombocytopenia, anemia, neutrophilic leukocytosis, monocytosis and eosinophilia dogs. Cats have less specific CBC findings but may have a transient anmia with persistent eosinophilia. Arthrocentesis (if polyarthritis suspected) in dogs revelas neutrophilic lymphocytic or mononuclear polyarthritis. IFA for igG confirms exposure. Blood or tissue culture is the most reliable test for a definitive diagnosis in cats but appears to be insensitive for the diagnosis of canine bartonellosis. To overcome this problem in dogs, a modified, insect t-based, culture medium (BAPGM) has been developed that can culture 7 different *Bartonella spp*. This can be combined with PCR to further enhance the diagnostic capabilities. Pre-antibiotic treatment samples are critical for an accurate diagnosis. PCR alone may be more sensitive than serology or standard culture in both cats and dogs.
[1,3,6,8,9]

Prevention — 212f

Control of arthropod vectors is the best form of prevention. Using flea and tick preventatives on dogs and flea preventatives on cats will significantly lower the risk of transmission to both people and pets. In endemic areas preventatives should be used year round. In young dogs a 10% imidocloprid/50% permethrin combination product used every 21 days has been found to be highly effective in the prevention of canine vector borne diseases in endemic areas so long as it is applied prior to first exposure. This product is toxic to cats and cannot be used in this species.
[3,12]

Prognosis — 212g

Variable depending on system affected. Aortic Valve Endocarditis carries a grave prognosis. Due to zoonotic implications and severity of disease symptoms prevention by avoiding

FIG. 8B CONTINUE

| Treatment | Comprehensive Treatment | Disease Highlights | Follow-up/Monitoring | Client Education | Latest Research | Prudent Use |

214

When platelet counts are used as a guage for clinical improvement, they should be rechecked 4 to 8 weeks post-treatment at the latest. Platelet counts increase rapidly after therapy and are typically normal within 14 days post-treatment. *E.canis* can persist despite extensive doxycycline therapy and recrudescence of clinical signs due to persistant infection is possible. Thus, ehrliciosis patients should be continually monitored (CBC's are of particular importance) on a regular basis even after a clinical response to therapy.

FIG. 8C

| Treatment | Comprehensive Treatment | Disease Highlights | Follow-up/Monitoring | Client Education | Latest Research | Prudent Use |

Client education revolves around preventative strategies. Clients should understand that while the disease in zoonotic, infected pets pose minimal risk as long as tickls are well controlled. Dogs serve bas sentinels for disease and thus an infected pet population serves as a reminder of the importance for adequate tick control in people as well. Clients need to be aware that E.canis can persist despite extensive doxycycline therapy and recrudescence of clinical signs due to persistant infection is possible. Long-term monitoring (regular CBC testing) is typically recommended.
[1,2,6]

| Treatment | Comprehensive Treatment | Disease Highlights | Follow-up/Monitoring | Client Education | Latest Research | Prudent Use |
|---|---|---|---|---|---|---|

A recent study on desmopressin acetate (DDAVP) to help ameliorate the hemorrhagic disorders associated with CME showed a significant improvement in platelet counts, bleeding times and fibrinogen levels. DDAVP has been shown to be an adjunct therapy for bleeding disorders cause be hemophilia. Von willbrand's Disease, Hepatopathies and NSAID toxicities. In the study, 1 microgram/kg was administered subcutaneously to dogs affected whit CME and shortened prolonged buccal mucosal bleeding times, increased platelet counts and fibrinigen concentrations. This may serve as a useful adjunct therapy especially in cases of chronic disease; however, result are preliminary and further research is needed.
[12]

FIG. 8E

| Treatment | Comprehensive Treatment | Latest Research | Associated Diagnoses | Prudent Use |

220

- Gingivostomatitis and Pharyngitis
- Periodontal Disease
- Abscess, Tooth Root
- Tooth Displacement Injury
- Tooth Fracture
- Fractured Mandible/Maxilla

IntuitiveVet - Search: "otitis"

beta.vet.timelesslabs.com/dashboard/module/internalmedicine/?systemID=6&diagnosisID=135&moduleID=1&speciesID=1 intuitive vet
evidence based decision support

Referrals | Feedback | Account | Logout

Q Diagnosis search...

- Home
- Canine Systems
- Feline Systems
- Library
- Help

Treatment | Comprehensive Treatment | Disease Highlights | Follow-up/Monitoring | Associated Diagnoses | Prudent Use — 222 are beyond the scope of this system. Antibiotics are used as an adjunct therapy with mandibular and maxillar fractures due to the higher possibility of bacterial contamination. They are typically only necessary if the fracture is open or contaminated and the incidence of osteomyelitis is lessened when antibiotics are used. There are 2 approved antibiotics for dental infections in North America: amoxicillin/clavulanate and clindamycin.

Prudent Use of Antimicrobials and Note from Development Team

A major goal of IntuitiveVet is to be one of the main agents supporting evidence based veterinary medicine. The IntuitiveVet knowledge base is continuously updated with the latest published evidence providing veterinarians with the latest developments in veterinary therapeutics. Currently, this system provides guidelines for antimicrobial, antifungal and anthelmintic usage in small animal veterinary medicine pratice. Our goal is to provide veterinarians with the most up-to-date, evidence based medicine in these fields.

Throughout the course of researching material for this system it became clear to us that there are significant gaps in objective, scientific published data in veterinary medicine. Accordingly, our guidelines are based on the current available data, along with expert opinion with consideration given to infectious disease and internal medicine principles. The treatment options provided should be considered a basis for decision making with the understanding that certain, special cases may require different or additional approaches. Our future endeavors include developing the system to include therapeutic guidelines for rival, autoimmune, neoplastic, endocrine and behavioral disorders to name few.

In this era of super-bugs and significant antimicrobial resistance it is important to select for appropriate antimicrobials in terms of class, dose and duration. Whenever possible, a culture and sensitivity should be performed to assess the appropriate choice of antibiotic. It is important, however, to make empirical antibiotic selections while awaiting culture (or in the event that culture is not possible). Helping veterinarians choose effective empirical therapies while minimizing resistance to antimicrobials to optimally protect animals and public health and preserve the therapeutic value of antimicrobial drugs is a major goal of this system.

Important Guides to Prudent Antimicrobial Therapy in Dogs and Cats
[Adapted from the Basic Guidelines of Judicious Therapeutic Use of Antimicrobials, August 1, 2006, by the American Association of Feline Practitioners and the American Animal Hospital Association, and Appropriate Empirical Antimicrobial Therapy: Making Decisions Without a Colture ACVIM 2009 by L Trepanier]

1. Antimicrobials should never be prescribed on a "just in case" basis as this adds unnecessary cost, may cause adverse effects (vomiting, diarrhea, inappetance) that can obscure the actual diagnosis and encourage the selection of resistance bacteria.

2. Strive to rule out non-bacterial causes of disease before initiating antibiotic therapy. Make sure there is good evidence of a bacterial infection prior to starting antimicrobial therapy (fever alone and/or leukocytosis alone are not justifications for antibiotic use). Fever with neutropenia is an established indication for antimicrobial use.

3. In the case of exudative conditions, cytology should be performed prior to antimicrobial selection.

| Tick Name | Common Name | Geographic Distribution | Agents Transmitted | Diseases Transmitted |
|---|---|---|---|---|
| *Amblyomma hebraeum* | South African Bont tick | Africa; | *Rickettsia africae;* | African tick bite fever; |
| *Amblyomma variegatum* | Variegated African tick | Sub-saharan Africa; South Arabia; Caribbean Islands; Indian Ocean; | *Rickettsia africae; Yellow fever virus;* | African tick bite fever; Yellow fever; |
| *Amblyomma hebraeum* | Marsh tick | Southwest England; Wales; | *Anaplasma phagogytophilum; Babesia canis; Babesia caballi; Babesia divergens; Borrelia burgdorferi; Rickettsia cononii;* | Human granulocytic ehrlichiosis; Canine babesiosis; Equip piroplasmosis; Bovine babesiosis "Redwater fever"; Lyme Disease; Mediterranean Spotted fever; |

| | | | |
|---|---|---|---|
| *Haemaphysalis leachi* | Yellow Dog tick | Africa; Asia; Australia; | *Coxiella burnetii*; *Babesia canis*; | Q fever; Canine babesiosis; |
| *Haemaphysalis longicornis* | Bush tick | East Asia; Australia; | *Coxiella burnetii*; *Babesia canis*; | Q fever; Canine babesiosis; |
| *Ixodes canisuga* | British dog tick | Europe; Asia; | *Babesia missiroli*; *Yersinia pestis*; | Badger babesiosis; Plague; |
| *Ixodes hexagonus* | Hedgehog tick | United Kingdom; Sweden; | *Borrelia burgdorferi*; *Theileria microtis*; *Theileria annae*; | Lyme Disease; Malaria-like disease in humans; Babesiosis-like disease in dogs; |

FIG. 8H CONTINUE

intuitiveVet
evidence based decision support

IntuitiveVet - Library

[Referrals] [Feedback] [Account] [Logout]

🔍 Diagnosis search...

Library — 276

Our library is akin to a living, breathing organism. It is constantly growing, constantly evolving and constantly updated. Every time we find and reference new studies or information on the material contained within IntuitiveVet it is updated and the library develops. If you are interested in having a contained within IntuitiveVet it is updated and the library develops. If you are interested in having a look at some of the sources we are referencing, please feel free to have a look around our library

Journals

| 🔍 | ▵ Journal |
|---|---|
| | American Journal of Animal and Veterinary Sciences |
| | American Journal of Orthodontics and Dentofacial Orthopedics |
| | American Journal of Pathology |
| | American Journal of Veterinary Research |
| | Anatomia Histologia Embryologia |
| | Antimicrobial Agents and Chemotherapy |
| | Archivos de medicina veterinaria |
| | Australian Veterinary Journal |
| | Clinical Techineques in Small Animal Practice |

Sidebar: Home, Canine Systems, Feline Systems, Library, Help, Admin

FIG. 10

| |
|---|
| Companion Animal |
| Comparative Clinical Pathology |
| Compendium: Continuing Education for Veterinarians |
| Dental Traumatology |
| DVD: The Newsmagazine of Veterinary Medicine |
| European Journal of Histochemistry |

FIG-10 CONTINUE intuitivevet
evidence based decision support

IntuitiveVet - Administration beta.vet.timelesslabs.com/admin/diagnosis/detail.php?id=230

| Fixes | Feedback | Users | Groups | Perms | Account | System | Logout |

Gastrointestinal/Hepatic/Pancreatic System —282

[Add Diagnosis ▽]

| | ◁ Species | Name |
|---|---|---|
| Del | Dog | Alaria canis and Alaria alata |
| Del | Dog | Apophallus venustus |
| Del | Dog | Ascocotyle (Phagicola) longa |
| Del | Dog | Balantidium coli |
| Del | Dog | Bartonellosis |
| Del | Dog | Campylobacter Enteritis |
| Del | Dog | Cholecystitis |
| Del | Dog | Cholelithiasis |
| Del | Dog | Clonorchis sinensis (Opisthorchis sinensis) |
| Del | Dog | Clostridial Enterocolitis |

284 — 280

Admin Home
Logs
Content
Manage Data
Modules
Systems
Diagnoses
Generic Meds
Combo Meds
Commercial Meds
References
Citations
Sources
Other

FIG - 11

| | | |
|---|---|---|
| Del | Dog | Coccidiosis (Cystoisospora) |
| Del | Dog | Colitis, acute |
| Del | Dog | Constipation (with Endotoxemia or fever) |
| Del | Dog | Cryptocotyle lingua |
| Del | Dog | Cryptosporidiosis |
| Del | Dog | Diarrhea, Acute |
| Del | Dog | Diarrhea, Antibiotic-Responsive |
| Del | Dog | Diphyllobothrium spp. |
| Del | Dog | Entamoeba historical (Amebiasis) |
| Del | Dog | Gall Bladder Rupture |

FIG-11 CONTINUE (280)

intuitivevet
evidence based decision support

IntuitiveVet - Administration beta.vet.timelesslabs.com/admin/diagnosis

Fixes | Feedback | Users | Groups | Perms | Account | System | Logout

- Admin Home
- Logs
- Content
- Manage Data
- Modules
- Systems
- Diagnoses
- Generic Meds
- Combo Meds
- Commercial Meds
- References
- Citations
- Sources
- Other

Diagnoses — 286

| | △Name | ▽Visible — 288 | Add Diagnosis |
|---|---|---|---|
| Go | | ◁▷ | |
| Edit | Abscess, lung | ◇ | |
| Edit | Abscess, Tooth Root | ◇ | |
| Edit | Abscesses, Cutaneous (Including Cat Bite Abscesses) | ◇ | |
| Edit | Aelurostrongylus abstrusus | ◇ | |
| Edit | Anal Sac Disease | ◇ | |
| Edit | Anaplasmosis | ◇ | |
| Edit | Angiostrongylus vasorum | ◇ | |
| Edit | Arthritis, Bacterial | ◇ | |
| Edit | Aspergillosis | ◇ | |

FIG_12A

| | | |
|---|---|---|
| Edit | Babesiosis | » |
| Edit | Balantidium coli | » |
| Edit | Bartonellosis | » |
| Edit | Bite Wound Infections | » |
| Edit | Bites, Snake | » |
| Edit | Bites, Spider | » |
| Edit | Blastomycosis | » |
| Edit | Borreliosis (Lyme Disease) | » |
| Edit | Brucellosis | » |

FIG. 12A CONTINUE intuitiveVet
evidence based decision support

IntuitiveVet - Administration beta.vet.timelesslabs.com/admin/diagnosis/detail.php?id=230

| Fixes | Feedback | Users | Groups | Perms | Account | System | Logout |

Admin Home
Logs
Content
Manage Data
Modules
Systems
Diagnoses
Generic Meds
Combo Meds
Commercial Meds
References
Citations
Sources
Other Topical Prescriptions ~292

Add Prescription ~296

290 {

| | Species | Order | Medication(s) | Dose | Route(s) | Frequency | Duration | Preferred |
|---|---|---|---|---|---|---|---|---|
| Edit Del | Dog | 1 | Miconazole | enough to coat the entire length of the ear canal otic application | topical | q12h | for 10-14d | ✓ |
| Edit Del | Dog | 6 | Ketoconazole | Ear cleaner otic application | topical | q24h | for 10-14d | ✓ |
| Edit Del | Dog | 2 | Clotrimazole | enough to coat the entire length of the ear canal otic application | topical | q12h | for 10-14d | ✗ |
| Edit Del | Dog | 3 | Nystatin | enough to coat the entire length of the ear canal otic application | topical | q12h | for 10-14d | ✗ |
| Edit Del | Dog | 4 | Thiabendazole | enough to coat the entire length of the ear canal otic application | topical | q12h | for 10-14d | ✗ |
| Edit Del | Dog | 5 | Silver sulfadiazine | enough to coat the entire length of the ear canal otic application | topical | q12h | for 10-14d | ✗ |

FIG-12B

| | | | | | | 290 | |
|---|---|---|---|---|---|---|---|
| Edit Del | Dog | 5 | Silver sulfadiazine | enough to coat the entire length of the ear canal otic application | topical | q12h | for 10-14d | ✗ |
| Edit Del | Dog | 1 | Miconazole | enough to coat the entire length of the ear canal otic application | topical | q24h | for 10-14d | ✓ |
| Edit Del | Dog | 2 | Neomycin/Nystatin/ Triamcinolone/Permethrin | 0.3ml | topical | q24h | for 10- | ✗ |

Systemic Prescriptions —294

1-8 of 8

[Add Prescription ▽]

| 🔍 | ▲Species | Order | Medication(s) | Dose | Route(s) | Frequency | Duration | Preferred —296 |
|---|---|---|---|---|---|---|---|---|
| Edit Del | Dog | 1 | Ketoconazole | 5-10 mg/kg | PO | q12-24h with food | for 1-2 weeks beyond cytological cure | ✓ |
| Edit Del | Dog | 2 | Fluconazole | 5-10 mg/kg | PO | q12-24h with food | for 1-2 weeks beyond cytological cure | ✗ |
| Edit Del | Dog | 3 | Itraconazole | 5-10 mg/kg | PO | q12-24h with food | for 1-2 weeks beyond cytological cure | ✗ |
| Edit Del | Dog | 1 | Ketoconazole | 5-10 mg/kg | PO | q12-24h with food | for 1-2 weeks beyond cytological cure | ✓ |

FIG. 12B CONTINUE

Generic Medication

| | Medication Name | Drug Classes | Trade Names |
|---|---|---|---|
| Go | | | |
| Edit | Acetic Acid/Boric Acid | | |
| Edit | Albendazole | | Valbazen, Albenza |
| Edit | Allopurinol | | Zyloric |
| Edit | Aluminum Acetate | | |
| Edit | Amikacin | Antibiotic | |
| Edit | Amitraz | | |
| Edit | Amoxicillin | Antibiotic | |
| Edit | Amoxicillin/Clavulanate | Antibiotic | Clavamox, Augmentin |
| Edit | Amphotericin B | | AmBisome, Fungizone IV |

FIG. 13A

| | | | 300 |
|---|---|---|---|
| Edit | Ampicillin | Antibiotic | |
| Edit | Amprolium | | Corid |
| Edit | Antivenin | | |
| Edit | Atovaquone | | Mepron |
| Edit | Azathioprine | Antibiotic | |
| Edit | Azithromycin | | Zithromax |
| Edit | Bacitracin/Neomycin/Polymyxin B | | Mycitracin |
| Edit | Benznidazole | | Ragonil |
| Edit | Benzoyl Peroxide | | |

FIG. 13A CONTINUE

Generic Medication Information

ID: 7
Name: Cefyovecin
Contraindications: Hypersensitivities rare but check for previous hypersensitivities to cefovecin or other beta-lactams. Anaphylaxis has been reported with this product. With renal failure reduce dose.
Drug Interactions: May increase active concentration of highly protein-bound drugs and increase risk of adverse reactions:
- carprofen
- furosemide
- doxycycline
- ketoconazole
- NSAIDs
- propofol
- cardiac medications
- anticonvulsants
- certains behavioral medications

FIG. 13B

Adverse Effects:
False positive glucosuria with "Clinitest"

Generally well tolerated, however, mild to moderate elevation in GGT, ALT, BUN and serum creatinine reported in some animals The most common adverse effects in decreasing order of frequency include:
- Dogs: depression/lethargy, anorexia, and vomiting
- Cats: anorexia, depression/lethargy, and vomiting
- Both: hypersensitivity rections are rare but can be severe including anaphylaxis and death.

This drug can have residual levels within the body for up to 65 days, thus when adverse events do occur, they need to be treated for prolonged periods.

Trade Names

| ▽ Trade Name |
|---|
| Convenia |

🔍 Edit     Add Trade Name

FIG. 13B CONTINUE

SOFTWARE TOOL FOR VETERINARIANS

CROSS-REFERENCE TO RELATED APPLICATIONS

This patent application claims priority under 35 USC §119(e) of U.S. provisional Application Ser. No. 61/679,360, filed on Aug. 3, 2012, the contents of which are hereby incorporated by reference.

TECHNICAL FIELD

The present invention relates to the field of diagnostic and treatment support tools for veterinarians.

BACKGROUND OF THE ART

The rapid growth of the effective medical knowledge base makes it difficult for health care providers to keep apprised of best practices and effectively deliver quality care. This is especially true for treatment techniques, medication, and testing procedures, which are continuously being developed. Moreover, proper health management is not only sought for humans but also for animals since pet owners are not only concerned with their own health but also with that of their pet.

Computer-based decision support systems have been developed to address these issues. However, known decision support systems take a broad range of variables as input and provide outputs that fail to precisely address a specific medical problem. For instance, such systems output lists of possibilities for diagnoses, treatments, and additional tests for rule outs, from which a user attempts to select an appropriate treatment.

Veterinarians experience significant time constraints in diagnosing and treating patients and there is currently lacking a comprehensive, up-to-date, evidence-based resource for immediate and effective access.

There is therefore a need for an improved veterinary decision support system and comprehensive web-based reference source.

SUMMARY

There is described herein a method and system for providing treatment options and detailed information about individual infectious diseases to veterinarians.

The system serves as a multi-reference resource and includes a drug formulary associated with each generated treatment, a clinical consult with specific information pertaining to each disease, a client education resource, a constantly updated reference library, and a clinician's toolbox (with relevant calculators and aids) to assist in the decision support process and time management for small animal veterinarians with respect to infectious diseases.

The system generates options for further information pertaining to each ailment, which comprises Comprehensive Treatment, Disease Highlights, Follow-up/Monitoring, Client Education, Latest Research, Associated Diagnosis, and Prudent Use all based on evidence-based research. Medical decisions are complex and thus practitioners require a wealth of information to assist with that process; however, they need this information sorted into an organized, retrievable, concise format. The information within this system may be presented in a tab format design.

In accordance with a first broad aspect, there is provided a system for generating treatment options and pertinent disease information for treating an animal of a first species suffering from an ailment, the system comprising a memory populated with a plurality of diagnoses each associated with at least a corresponding one of a plurality of treatment protocols each adapted for treating at least one animal species and at least one ailment, each one of the plurality of treatment protocols supported by evidence-based research, a processor, and at least one application stored in the memory and executable by the processor for receiving input data representative of a diagnosis of the ailment for the first species, retrieving from the memory the at least one treatment protocol associated with the diagnosis as received, and outputting the retrieved at least one treatment protocol.

Still further in accordance with the present application, the at least one application is executable for receiving medical data comprising at least one of a symptom, an affected body site, and a diagnostic test result, retrieving from the memory the plurality of diagnoses, comparing the received medical data to the plurality of diagnoses for establishing a tentative diagnosis for the animal, and outputting the tentative diagnosis.

Still further in accordance with the present application, the at least one application is executable for receiving the input data indicative of a validation of the tentative diagnosis.

Still further in accordance with the present application, the memory is populated with at least one rule applicable for determining the at least one corresponding treatment protocol adapted for treating the at least one animal species and the at least one ailment and further wherein the at least one application is executable for retrieving the at least one rule from the memory and applying the at least one rule to the input data for retrieving the at least one treatment protocol associated with the diagnosis as received.

Still further in accordance with the present application, the memory is populated with at least one fuzzy rule having at least one instruction associated therewith and further wherein the at least one application is executable for applying fuzzy logic to execute the at least one instruction.

Still further in accordance with the present application, the at least one application is executable for receiving the input data comprising at least one parameter selected from the group consisting of an age of the animal, a health condition of the animal, and a drug therapy currently prescribed to the animal, and further wherein the memory is populated with at least one exclusion rule applicable for excluding a selected one of the plurality of treatment protocols if the at least one parameter meets a predetermined criterion.

Still further in accordance with the present application, the at least one application is executable for associating a risk with the selected one of the plurality of treatment protocols if the predetermined criterion is met and for outputting an alert indicative of the risk.

Still further in accordance with the present application, the memory is populated with therapy information associated with each one of the plurality of treatment protocols, the therapy information comprising at least one of an identification of a drug, a dosage of the drug, a route of administration of the drug, a duration of administration, a frequency of administration, a contraindication of the drug, and an adverse effect of the drug, and further wherein the at least one application is executable for retrieving the therapy information associated with the at least one treatment protocol associated with the diagnosis and outputting the retrieved therapy information.

Still further in accordance with the present application, the at least one application is executable for establishing on the basis of the retrieved therapy information a ranking of the at least one treatment protocol associated with the diagnosis and for outputting the ranking.

In accordance with another broad aspect, there is also provided a computer-implemented method for generating treatment options and pertinent disease information for treating an animal of a first species suffering from an ailment, the method comprising executing on a processor program code for receiving input data representative of a diagnosis of the ailment for the first species, retrieving from a memory at least one treatment protocol associated with the diagnosis as received, the memory populated with a plurality of diagnoses each associated with at least a corresponding one of a plurality of treatment protocols each adapted for treating at least one animal species and at least one ailment, each one of the plurality of treatment protocols supported by evidence-based research, and outputting the retrieved at least one treatment protocol.

Still further in accordance with the present application, medical data is received, the medical data comprising at least one of a symptom, an affected body site, and a diagnostic test result, retrieving from the memory the plurality of diagnoses, comparing the received medical data to the plurality of diagnoses for establishing a tentative diagnosis for the animal, and outputting the tentative diagnosis.

Still further in accordance with the present application, receiving the input data comprises receiving the input data indicative of a validation of the tentative diagnosis.

Still further in accordance with the present application, retrieving the at least one treatment protocol associated with the diagnosis comprises retrieving from the memory at least one rule applicable for determining the at least one corresponding treatment protocol adapted for treating the at least one animal species and the at least one ailment and applying the at least one rule to the input data.

Still further in accordance with the present application, retrieving the at least one treatment protocol associated with the diagnosis comprises applying fuzzy logic to execute at least one instruction associated with the at least one rule.

Still further in accordance with the present application, receiving the input data comprises receiving at least one parameter selected from the group consisting of an age of the animal, a health condition of the animal, and a drug therapy currently prescribed to the animal, and further wherein applying the at least one rule comprises applying at least one exclusion rule applicable for excluding a selected one of the plurality of treatment protocols if the at least one parameter meets a predetermined criterion.

Still further in accordance with the present application, a risk is associated with the selected one of the plurality of treatment protocols if the predetermined criterion is met and an alert indicative of the risk is output.

Still further in accordance with the present application, therapy information associated with the at least one treatment protocol associated with the diagnosis is retrieved from the memory and the retrieved therapy information is output, the memory populated with therapy information associated with each one of the plurality of treatment protocols, the therapy information comprising at least one of an identification of a drug, a dosage of the drug, a route of administration of the drug, a duration of administration, a frequency of administration, a contraindication of the drug, and an adverse effect of the drug Still further in accordance with the present application, a ranking of the at least one treatment protocol associated with the diagnosis is established on the basis of the retrieved therapy information and the ranking is output.

Still in accordance with another broad aspect, there is also provided a computer readable medium having stored thereon program code executable by a processor for generating treatment options and pertinent disease information for treating an animal of a first species suffering from an ailment, the program code executable for receiving input data representative of a diagnosis of the ailment for the first species, retrieving from a memory at least one treatment protocol associated with the diagnosis as received, the memory populated with a plurality of diagnoses each associated with at least a corresponding one of a plurality of treatment protocols each adapted for treating at least one animal species and at least one ailment, each one of the plurality of treatment protocols supported by evidence-based research, and outputting the retrieved at least one treatment protocol.

BRIEF DESCRIPTION OF THE DRAWINGS

Further features and advantages of the present invention will become apparent from the following detailed description, taken in combination with the appended drawings, in which:

FIG. 2a is a schematic diagram of a veterinary decision support system in accordance with an illustrative embodiment of the present invention;

FIG. 4b is a flowchart of the step of receiving medical data of FIG. 4a;

FIG. 4c is a flowchart of the step of applying treatment decision logic of FIG. 4a;

FIG. 4d is a flowchart of the step of providing a treatment option of FIG. 4a;

FIG. 5 is a screen capture of a user interface showing a welcome page in accordance with an illustrative embodiment of the present invention;

FIG. 7a is a screen capture of a user interface showing a diagnostic output in accordance with an illustrative embodiment of the present invention;

FIG. 7b is a screen capture of a user interface showing a treatment output with both topical and systemic treatment options in accordance with an illustrative embodiment of the present invention;

FIG. 7c is a screen capture of a user interface showing a treatment option warning screen in accordance with an illustrative embodiment of the present invention;

FIG. 7d is a screen capture of a user interface showing a form for flagging the treatment option of FIG. 7c;

FIG. 8a is a screen capture of a user interface showing the Comprehensive Treatment tab for a diagnosis output in accordance with an illustrative embodiment of the present invention;

FIG. 8b is a screen capture of a user interface showing the Disease Highlights tab for a diagnosis output in accordance with an illustrative embodiment of the present invention;

FIG. 8c is a screen capture of a user interface showing the Follow-up/Monitoring tab for a diagnosis output in accordance with an illustrative embodiment of the present invention;

FIG. 8d is a screen capture of a user interface showing the Client Education tab for a diagnosis output in accordance with an illustrative embodiment of the present invention;

FIG. 8e is a screen capture of a user interface showing the Latest Research tab for a diagnosis output in accordance with an illustrative embodiment of the present invention;

FIG. 8f is a screen capture of a user interface showing the Associated Diagnoses tab for a diagnosis output in accordance with an illustrative embodiment of the present invention;

FIG. 8g is a screen capture of a user interface showing the Prudent Use tab for a diagnosis output in accordance with an illustrative embodiment of the present invention;

FIG. 8h is a screen capture of a user interface showing the an information table tab (in this case, the European/Asian/African/Australian Ticks table) for a diagnosis output in accordance with an illustrative embodiment of the present invention;

FIG. 9 is a screen capture of a user interface showing diagnostic search results in accordance with an illustrative embodiment of the present invention;

FIG. 10 is a screen capture of a user interface showing a reference library in accordance with an illustrative embodiment of the present invention;

FIG. 11 is a screen capture of an administrative user interface showing a list of possible diagnoses affecting an animal in the Gastrointestinal/Hepatic/Pancreatic system in accordance with an illustrative embodiment of the present invention;

FIG. 12a is a screen capture of an administrative user interface showing a list of all possible diagnoses affecting an animal in accordance with an illustrative embodiment of the present invention;

FIG. 12b is a screen capture of an administrative user interface showing a list of possible prescriptions for treating an animal with a specific diagnosis of 12a;

FIG. 13a is a screen capture of an administrative user interface showing a list of medications for use in treating a given diagnosis in accordance with an illustrative embodiment of the present invention; and FIG. 13b is a screen capture of an administrative user interface showing information about a specific one of the medications of FIG. 13a.

It will be noted that throughout the appended drawings, like features are identified by like reference numerals.

DETAILED DESCRIPTION

Figure 1:
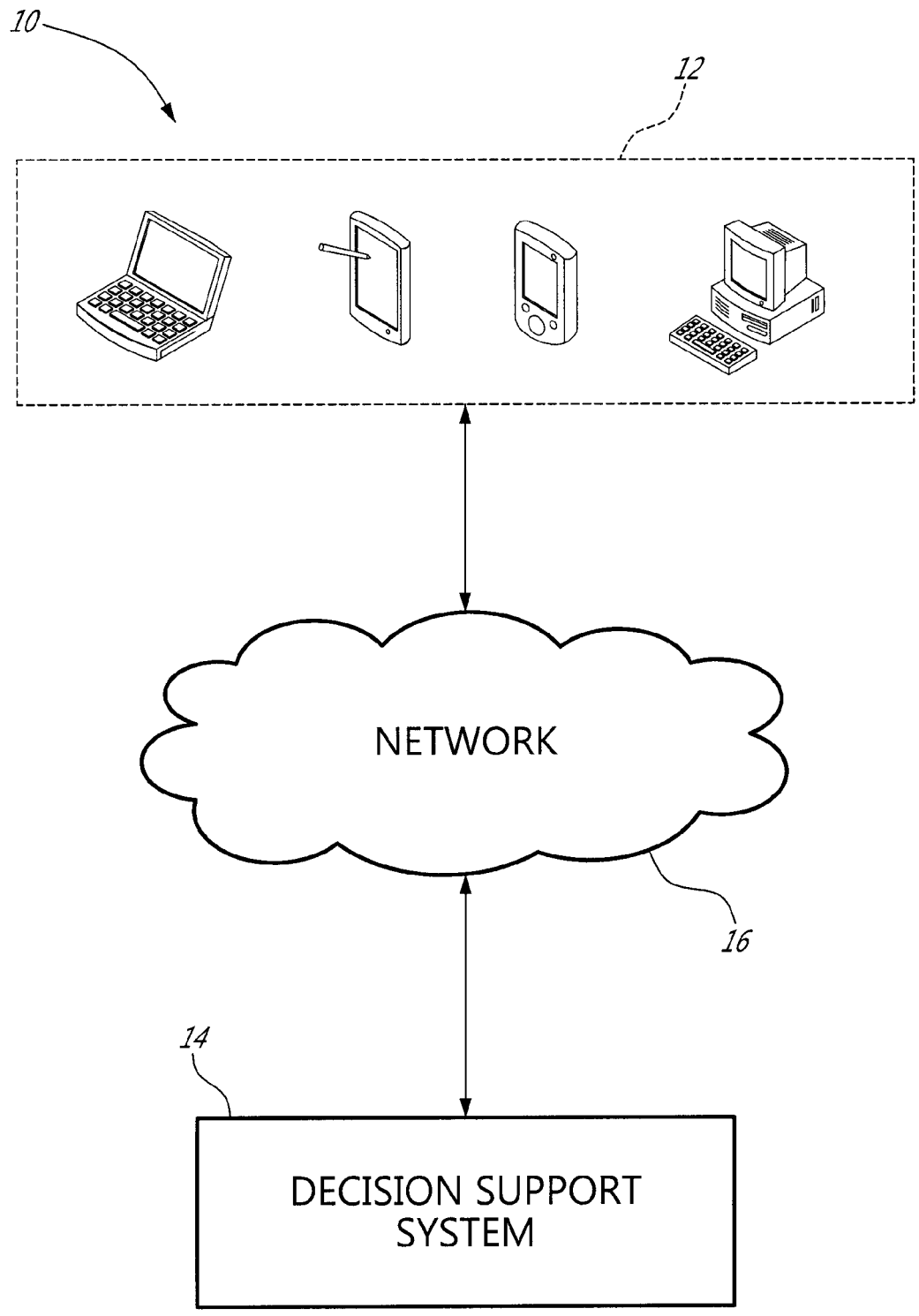
FIG. 1 is a schematic diagram of a system for providing veterinarians treatment options for treating ailing animals in accordance with an illustrative embodiment of the present invention.

Referring to FIG. 1, a communication system 10 for providing health care providers, illustratively veterinarians, with support in managing the health care of ailing animals will now be described. The system 10 comprises a plurality of devices as in 12 adapted to communicate with a decision support system 14 over a network 16. The devices 12 comprise any device, such as a personal computer, a personal digital assistant, a smart phone, or the like, which is configured to communicate over the network 16, such as the Internet, the Public Switch Telephone Network (PSTN), a cellular network, or others known to those skilled in the art. Although illustrated as being separate and remote from the devices 12, it should be understood that the decision support system 14 may also be integrated with the devices 12, either as a downloaded software application, a firmware application, or a combination thereof.

Referring now to FIG. 2a, the decision support system 14 illustratively comprises a user interface 18 through which the user may interact with the decision support system 14. In particular and as will be discussed in further detail herein below, the user (e.g. a veterinarian) may use the user interface 18 to submit information to the decision support system 14. The decision support system 14 further comprises a processor 20, which may be any device that can perform operations on data. Examples are a central processing unit (CPU), a front-end processor, a microprocessor, a graphics processing unit (GPU/VPU), a physics processing unit (PPU), a digital signal processor, and a network processor. A plurality of applications 22a . . . 22n are illustratively running on the processor 20 for performing operations required at the processor 20 in order to provide treatment options to the user based on the information entered via the user interface 18. It should be understood that while the applications 22a . . . 22n presented herein are illustrated and described as separate entities, they may be combined or separated in a variety of ways.

The processor 20 is in communication with a memory 24, which may include one or more storage mediums, including a hard-drive, permanent memory such as Read-Only Memory (ROM), semi-permanent memory, such as Random Access Memory (RAM), cache, or the like. The memory 24 illustratively comprises a diagnostic database 26 and a treatment database 28. Again, it should be understood that although the databases 26 and 28 are illustrated and described as separate entities, they may be combined. For example, a single database may comprise a central table storing all diagnoses and another central table storing all medications. All systems and treatments would therefore reference the diagnosis and medication tables. Data may be entered into the database(s) through a series of field-based forms. Through these forms, the data is parsed and organized on entry into its appropriate table.

The diagnostic database 26 has stored therein information that may be used to diagnose a specific condition or disease in an animal of a given species, such as a cat or a dog, based on the information entered via the user interface 18. The stored information may comprise a list of symptoms, diagnostic test results, and/or affected body systems (i.e. body locations) and a list of known small animal diseases, as well as a correlation between the two lists. Using diagnostic algorithms and specifying symptoms and affected body systems, as well as input from various diagnostic test results allows for the generation of given diseases to aid in the diagnosis of the ailment. Given diseases can be further narrowed by the additional input of further diagnostic test results as they are performed, tailoring the diagnosis for the individual patient. The diagnostic database 26 can then be linked to the treatment database 28 making it possible to identify the type of therapy based on a diagnosis of the animal's condition.

The treatment database 28 may illustratively store rules and rule sets which are selected and executed according to the information provided by the user via the user interface 18 to respectively provide infectious disease therapy options to the veterinarian for curing the animal's condition, as will be discussed further below. In particular, the rules and rule sets may be stored with instructions indicating when the rules are to be selected and executed. They detail which treatments are best suited to treat a particular ailment on a per-location basis and may include, for example, medication usage criteria and decision trees. Rules to exclude the use of certain treatment based on variables, such as age, health issues or conditions, and/or drug therapy, are further provided. The rules and rule sets are illustratively based on available literature, such as trade magazines, and published, evidence-based veterinary practices and guidelines.

Figure 2B:
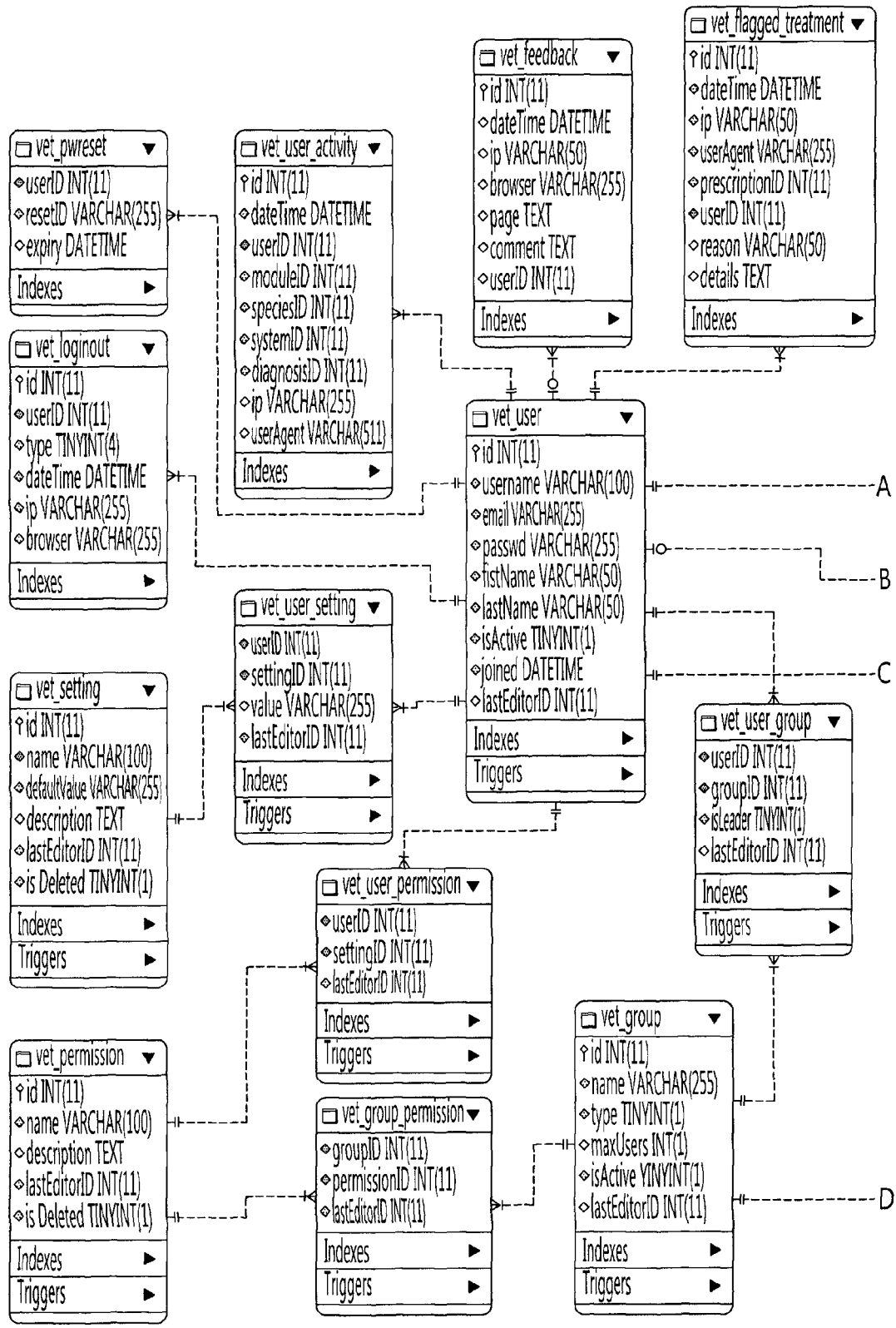
FIG. 2b is an exemplary database schema for a database of the decision support system.

FIG. 2b is an exemplary schematic of a database based on a relational-database which references objects through foreign keys. This embodiment allows the system to be scalable and extensible as the use and functionalities are increased.

Figure 3:
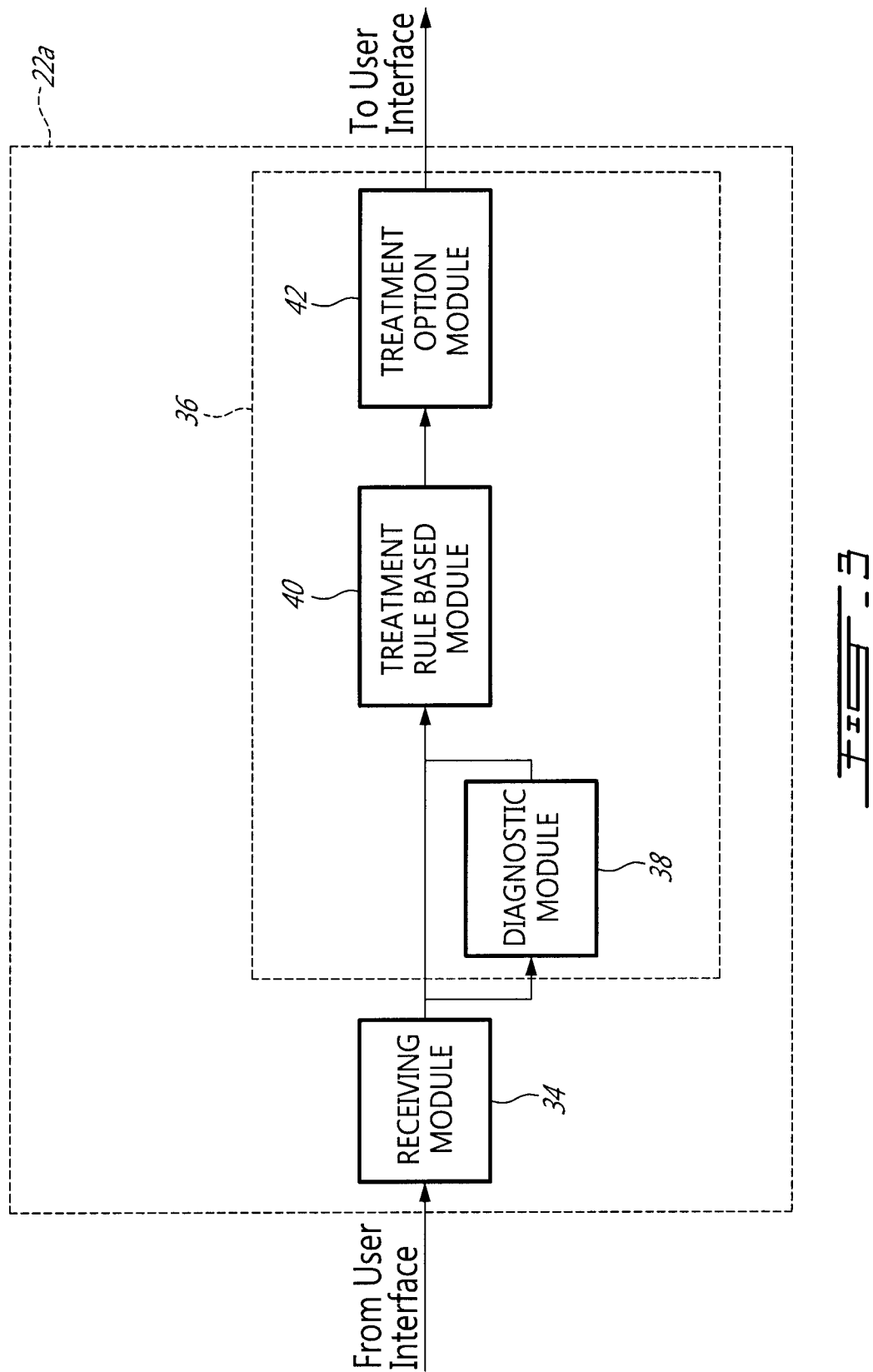
FIG. 3 is a schematic diagram of a processing application in accordance with an illustrative embodiment of the present invention.

Referring now to FIG. 3, a receiving module 34 illustratively receives the medical information, which is entered by a user via the user interface 18 for describing a specific case. Upon receipt of this information, the receiving module 34 transfers the medical data to an inference engine 36 which will generate options of appropriate treatment(s) to use in the particular context described. For this purpose, the inference engine 36 may illustratively comprise a diagnostic module 38, and a treatment rule based module 40.

If the information entered via the user interface 18 does not include a diagnosis of the animal's condition, the receiving module 34 first transfers the medical information to the diagnostic module 38, which analyzes this medical data to provide a diagnosis, as will be discussed in further detail below. Otherwise, the diagnostic module 38 is not involved in the process and need not come up with the diagnosis as the latter is included in the received medical information. Detection of the need for diagnosis may be performed automatically by the receiving module 34 by inspecting the received medical information for diagnostic data. Alternatively, detection of the need for diagnosis may result from a manual setting by the user. For example, the user may specify via the user interface 18, e.g. by ticking a checkbox, entering data in a text box, or selecting an appropriate item from a list presented in a drop-down box (none shown), that a diagnosis needs to be established based on the entered medical information.

Once the diagnosis is provided by the diagnostic module 38 or retrieved from the received medical data, the type of therapy sought is determined accordingly and the medical information is subsequently transferred to the treatment rule based module 40. Such rule based module 40 then uses a combination of discrete and fuzzy logic to generate the appropriate treatment options, which are then sent to the treatment option module 42 for display on the user interface 18. Although illustrated as comprising two rule based modules 38 and 40, the inference engine 36 may comprise fewer (e.g. one) or more of such modules 38 and 40, depending on the type of diagnosis or therapy sought for curing the animal's ailment. Accordingly fewer or more of the diagnostic database 26 and the treatment database 28 may be provided. Indeed, although two embodiments are described herein, namely for seeking diagnosis and infectious disease therapy, it will be apparent that additional embodiments may be provided for diagnosing or treating other conditions not discussed herein.

In particular, when an input vector comprising medical data describing the case under consideration is entered into the decision support system 14, the diagnostic rule based module 38 and the treatment rule based module 40 of the inference engine 36 respectively query the rules and rule sets stored in the diagnostic database 26 and the treatment database 28. Each of the rules and the instructions associated therewith may be evaluated by applying fuzzy logic and executed to generate a fuzzy result, i.e. an output described in terms of membership in fuzzy sets. Each output set illustratively represents a set of treatment options to be displayed to the user on the user interface 18. Since the rules and rule sets are based on available literature and published veterinary practices, the displayed diagnoses or treatment options are linked to relevant medical information for selective use by the veterinarian.

In summary, all treatment outputs are linked to a specific diagnosis through the treatment rule-based module 40. Diagnoses are organized into one or more systems, and systems into one or more modules. This allows diagnoses to be reused throughout the system in many different contexts. The method for retrieving a set of treatments for a given diagnosis is therefore a lookup of the treatment database 28 and may include processing of data through the inference engine 36 for any prescriptions linked to the given diagnosis.

Illustratively, any known communication protocols that enable devices within a computer network to exchange information may be used to enable communication between the various components of the system 10. Examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), SSH (Secure Shell Remote Protocol).

Figure 4A:
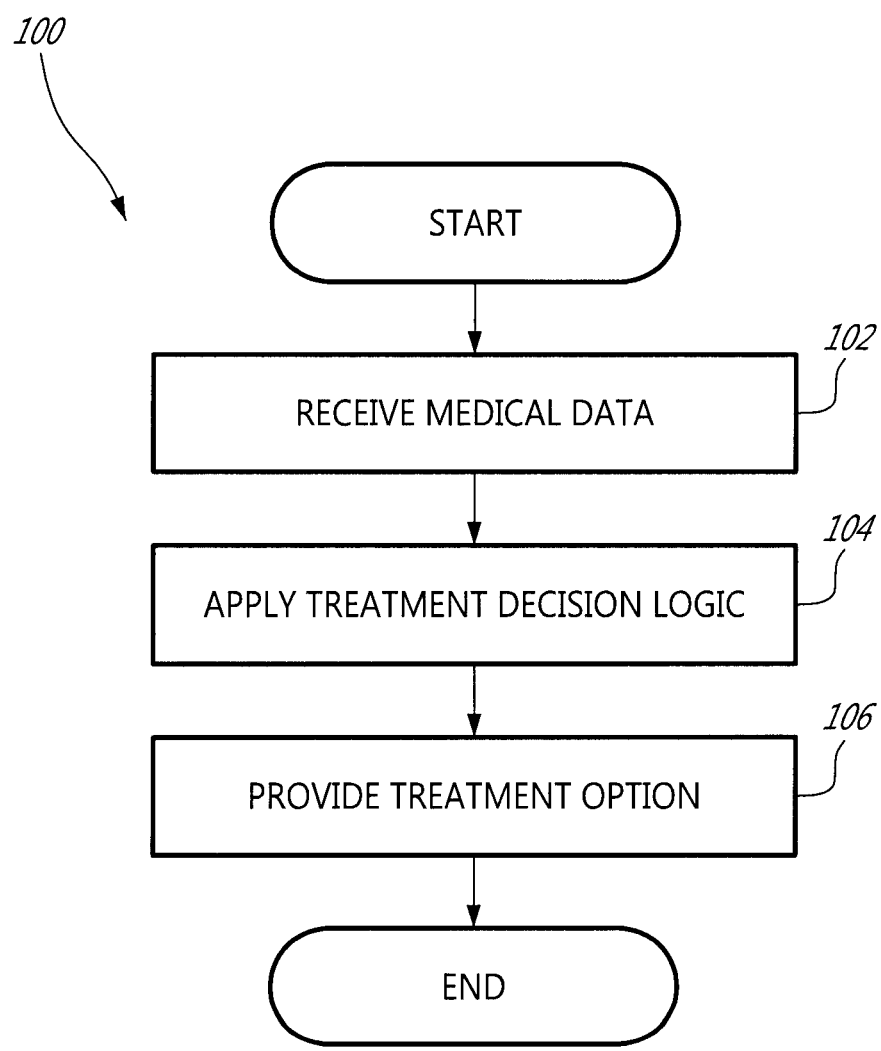
FIG. 4a is a flowchart of a method of providing treatment options in accordance with an illustrative embodiment of the present invention.

Referring now to FIG. 4a, a method 100 of providing veterinarians with support in managing the health care of ailing animals will now be described. A first step 102 of the method 100 comprises receiving medical data related to a specific case. The medical data illustratively comprises characteristics of the case, which may be provided by the veterinarian through the user interface 18 of the device 12. For this purpose, the user illustratively registers with a website associated with the decision support system 14 by creating a unique profile. Once registered, the user is provided with a unique identifier associated with his/her profile. The user may then access the decision support system 14 by logging on to the website using the unique identifier. Alternatively, the decision support system 14 may be installed on the device 12 as a software application, which may be launched by the user on the device 12 for accessing the decision support system 14.

Once the user has accessed the decision support system 14, he/she enters the medical data through the user interface 18. In order to ease the input process, a plurality of user interface control elements, such as drop-down boxes and menus (not shown), which may present a list of variables (e.g. animal's age, symptoms, etc.) related to the characteristics of the case are illustratively presented to the user on the user interface 18. Alternatively, text boxes may be also be used as input means. In this manner, by selecting the appropriate elements from the user interface control elements, the user is able to precisely describe the animal's medical problem. This can done by for example specifying, if known, the name of the specific disease, bacteria, fungus, virus or parasite affecting the animal, the body system (e.g. gastrointestinal or respiratory) or body location affected, as well as any additional details regarding the animal's symptoms. For example, if the animal is scratching and has red blotches on its skin and no additional testing has been effected on the animal and the veterinarian does not know the specific disease or bacteria involved, he/she may specify the body system affected, namely the skin, by selecting the "Dermatological" system from the drop-down menu 166*a* displayed on the user interface 18. Once the medical data is received at step 102, the next step (step 104) is to apply treatment decision logic in order to subsequently provide a treatment option at step 106.

In some embodiments, a treatment is broken up into its logical base elements when presented to the user. For example, a diagnostic prescription may consist of a medication, dosage range, series of administrable routes, frequency, and duration. The output may be formatted based on a predetermined standard applied to all treatment options as output, regardless of how the data is input into the system. Standardization is provided to ensure that information is not missed when providing the treatment option to the user, in addition to ensuring clarity and completeness to the process.

Figure 4B:
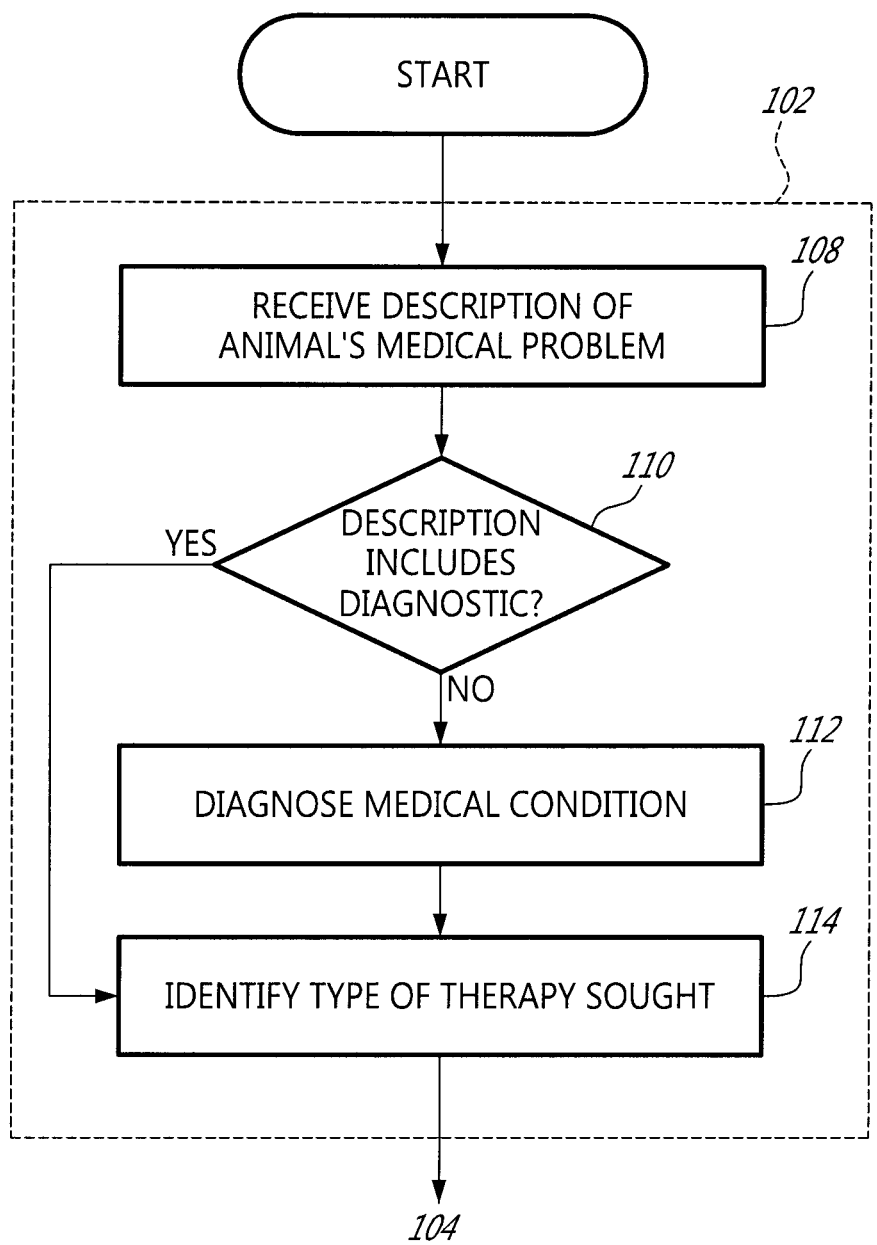

Referring now to FIG. 4*b*, in one embodiment, step 102 comprises receiving a description of the animal's medical issue through the user interface 18 (step 108) then assessing whether a diagnostic of the animal's condition has already been provided as part of the description (step 110). If the diagnostic is not part of the received medical data describing the animal's medical problem, the next step (step 112) is to diagnose the animal's condition based on the received data. In this case, the decision support system 14 compares the received medical data, and particularly the specified symptoms and/or body site, to entries stored in the diagnostic database 26 and establishes a tentative diagnosis of the most likely infectious diseases. In one embodiment, this tentative diagnosis may subsequently be presented to the user via the user interface 18 for validation prior to providing the treatment options. If the diagnosis is validated, the process of generating the treatment options based on the tentative diagnosis may then be initiated. If the user subsequently collects additional information, such as laboratory results, he/she may enter this information into the decision support system 14 via the user interface 18 and a more precise diagnosis and thus treatment decision may be provided by the decision support system 14 if necessary. In this manner, users may be provided with a tentative diagnosis and begin treatment while still waiting for more specific laboratory information.

Once the diagnosis is established, or alternatively if the diagnosis was already known and retrieved from the received description of the animal's medical problem, the next step is to query the treatment database 28 to identify from the received information the type of therapy sought (step 114) among the available infectious disease therapy solutions. This may be done using the correlation between each diagnostic entry and the corresponding type of therapy, which is stored in the treatment database 28, as discussed above.

Figure 4C:
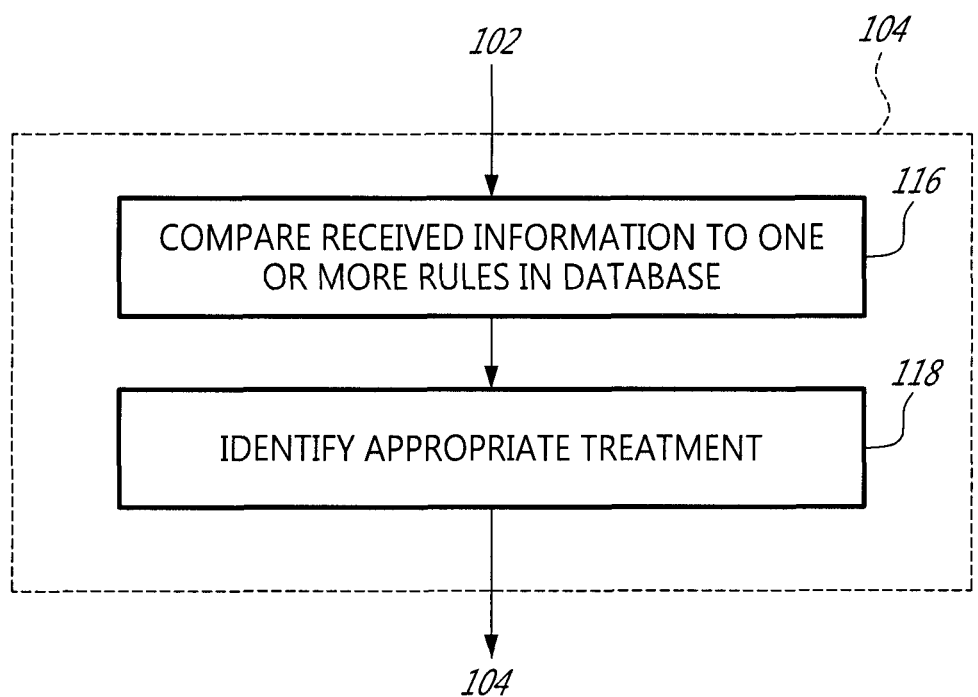
Figure 40:
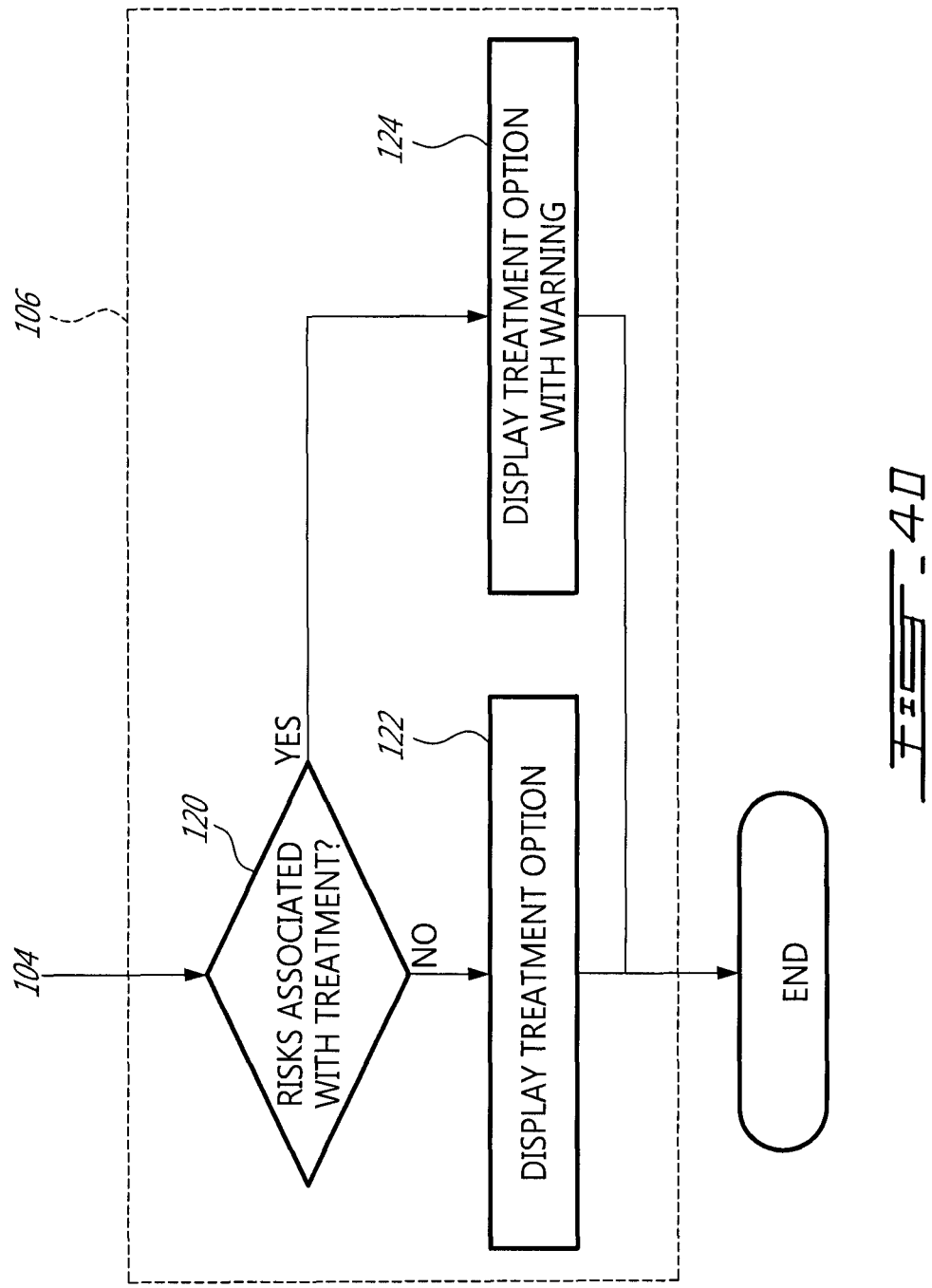

Referring now to FIG. 4*c*, once the type of therapy has been identified, the received information is compared at step 116 to one or more rules in the treatment database 28 corresponding to the identified therapy type. Upon applying the rules, the treatment appropriate for the specific medical problem in question is then identified at step 118.

Referring now to FIG. 4*d*, according to one embodiment, once the appropriate treatment is identified, the next step (step 120) is to determine, based on the received medical information, whether there is a potential risk with the treatment. This is done by further comparing the treatment option to rules stored in the treatment database 28 depending on the type of therapy sought. A risk relates to contraindications, drug interactions or adverse effects of the proposed treatment given the specific context of the case (e.g. animal's age or drug therapy currently used on the animal). If no risk is identified, the treatment option is directly displayed on the user interface 18 (step 122). Otherwise, the treatment option is displayed along with a warning (step 124), which alerts the user of the risk associated with the treatment option. Color coding may be used to present warnings, which may not only be visual but also audible. In this manner, users are able to make informed decisions as to whether the treatment option should be followed or not. Although the treatment option is illustrated herein as being displayed on the user interface 18, alternative delivery methods, such as sending a text message, an instant message, an email, or the like, may be used.

Referring now to FIG. 5, the user may log into the website or launch the application associated with the decision support system (reference 14 in FIG. 1), as discussed above. The user is then presented with a welcome page 150 on which options may be shown, such as for choosing the animal species for which therapy is sought or specifying the type of therapy sought, if known. In particular, the page 150 may be comprised of the following: relevant news, articles, development information, and videos. A side navigation section 152 contains links to the homepage 152*a* (as depicted in FIG. 5), species specific modules 152*b* and 152*c*, library of references 152*d*, help information 152*e* and administrative content management system 152*f*, described in more detail below. For example, the user may be presented with the option 152*b* for applying the decision support system 14 to canines and the option 152*c* for applying the decision support system 14 to felines. Although options related to two animal species are illustrated as being presented to the user, it should be understood as discussed above, that therapy may be sought for additional animal species. A top navigation bar 154 contains links to colleague referrals 154*a*, feedback about the system 154*b*, account details 154*c*, and logging off the system 154*d*. The top navigation bar 154 further contains a diagnostic search bar 156. The navigation bars as in 152, 154 described herein may consist of fewer or more navigational options than listed.

Figure 6A:
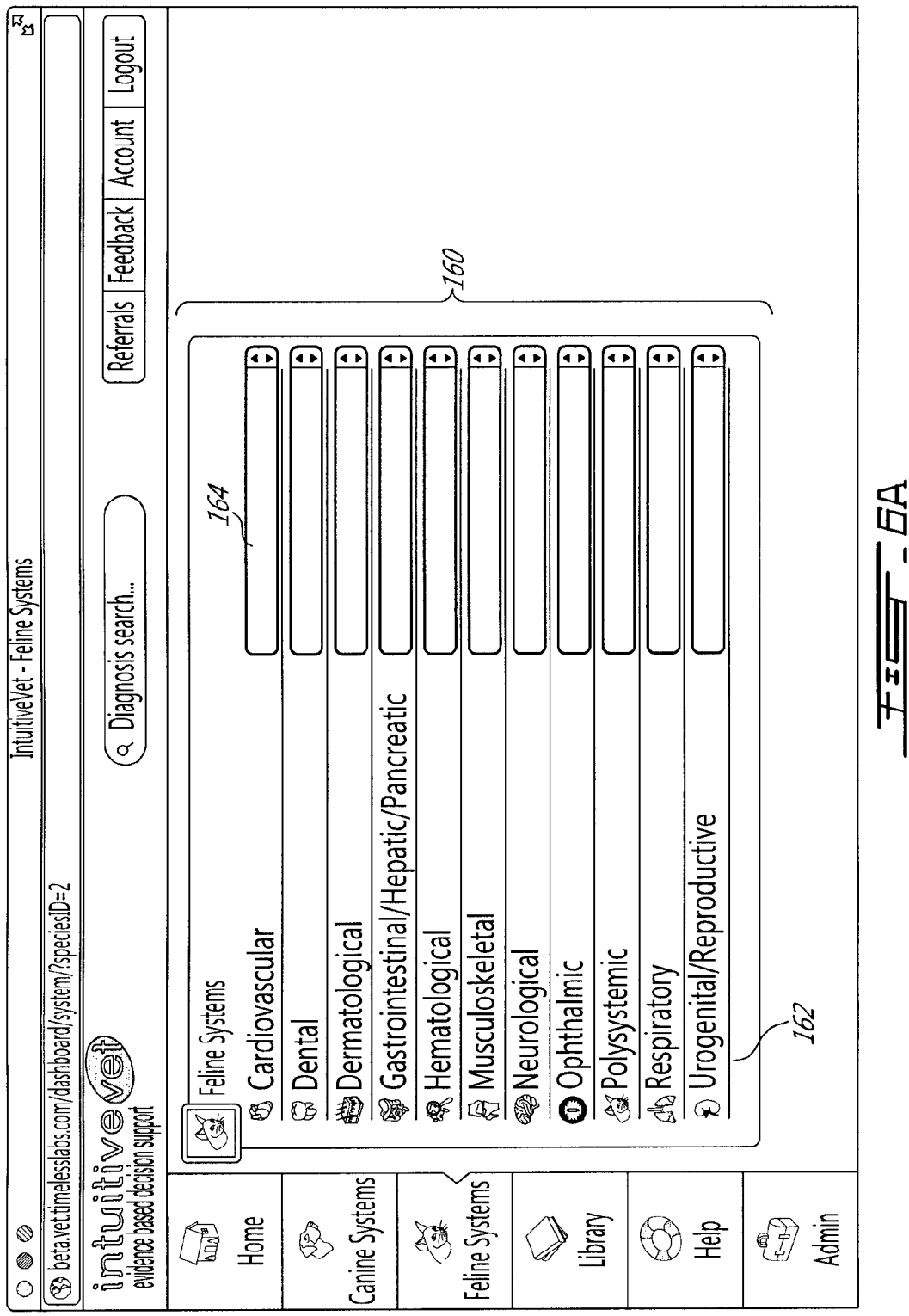
FIG. 6a is a screen capture of a user interface showing a list of feline systems and their corresponding diagnoses (in drop-down boxes) in accordance with an illustrative embodiment of the present invention.

Referring now to FIG. 6*a*, the user interface 18 presents the user with a system selection page 160. The system selection page 160 consists of a list of systems 162 applicable to the given species, in this case feline, and a list of each system's corresponding possible diagnoses in a drop-down menu 164. A user selects a diagnosis from a drop-down menu 164, which is passed to the receiving module 34. The treatment rule based module 40 processes the diagnosis against any rules that may apply and generates a set of treatment options through the treatment option module (reference 42 in FIG. 3), which are then presented to the user via the user interface (reference 18 in FIG. 2*a*). The animal species may be provided to the decision support system 14 by the user selecting a corresponding option on the user interface 18, as discussed herein.

Moreover, when therapy is sought for different animal species, rule mappings comprising different rules and rule sets between different input and output variables may be used to generate distinct sets of treatment options (see FIG. 7*a*, reference 182). As such, the numbers and types of rules and input and output variables may vary for each animal species. Moreover, information, such as notes and warnings, which may be presented to the user along with a set of treatment options 182 generated by the decision support system 14 may vary.

Figure 6B:
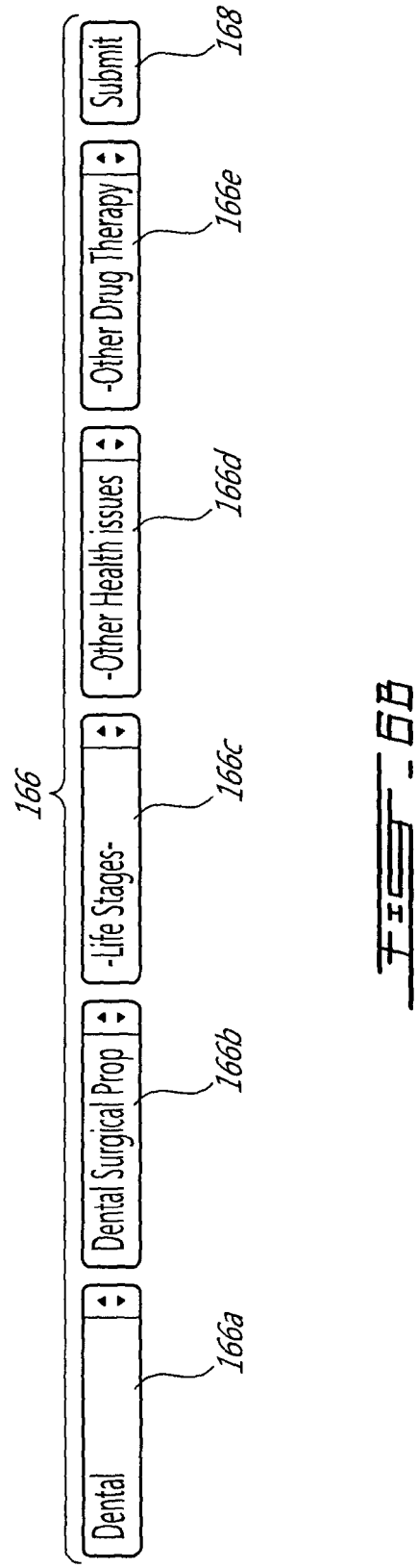
FIG. 6b is a screen capture of a user interface showing a data entry form for treating and animal seeking therapy in accordance with an illustrative embodiment of the present invention.

Referring now to FIG. 6b, once the information specifying the type of body systems and their associated diagnoses as well as the medications and other treatments that may be provided to cure the specified diagnosis have been entered by a system administrator and stored in the diagnostic database 26 and the treatment database 28, a user may then access the decision support system 14 to obtain therapeutic decision support. The user may be prompted to describe the animal's problem by providing details 166 related for example to the "Body System" 166a, e.g. dental, "Diagnosis" 166b, e.g. dental surgical prophylaxis, "Life Stages" 166c, "Other Health Issues" 166d and "Other Drug Therapy" 166e. Once the user has entered all of the relevant information pertaining to the case, the "Submit" option 168 may then be selected in order for the decision support system 14 to run the calculations and comparisons that will serve as a basis for making treatment options.

The rule sets stored in the diagnostic database 26 and the treatment database 28 are illustratively applied to filter treatments not suitable for the given inputs: age 166c, if any, other health issues 166d, if any, and other drug therapy 166e, if any, which relate to the current case. For example, a fuzzy rule may be written to avoid the drug output if the animal's age is less than 3 months. In this manner, upon applying the rules, the drug may not be presented to the user as part of the set of treatment options 182 if the animal for which therapy is sought is indeed less than 3 months of age. It should also be understood that different rule mappings may be used when different therapies are sought.

Any calculations run through the decision support system 14 are further stored in the memory 24 for record keeping purposes and statistical analysis. This allows the decision support system 14 to track the frequency at which users access the decision support system 14, as well as which body systems and diagnoses are most commonly processed.

Figure 6C:
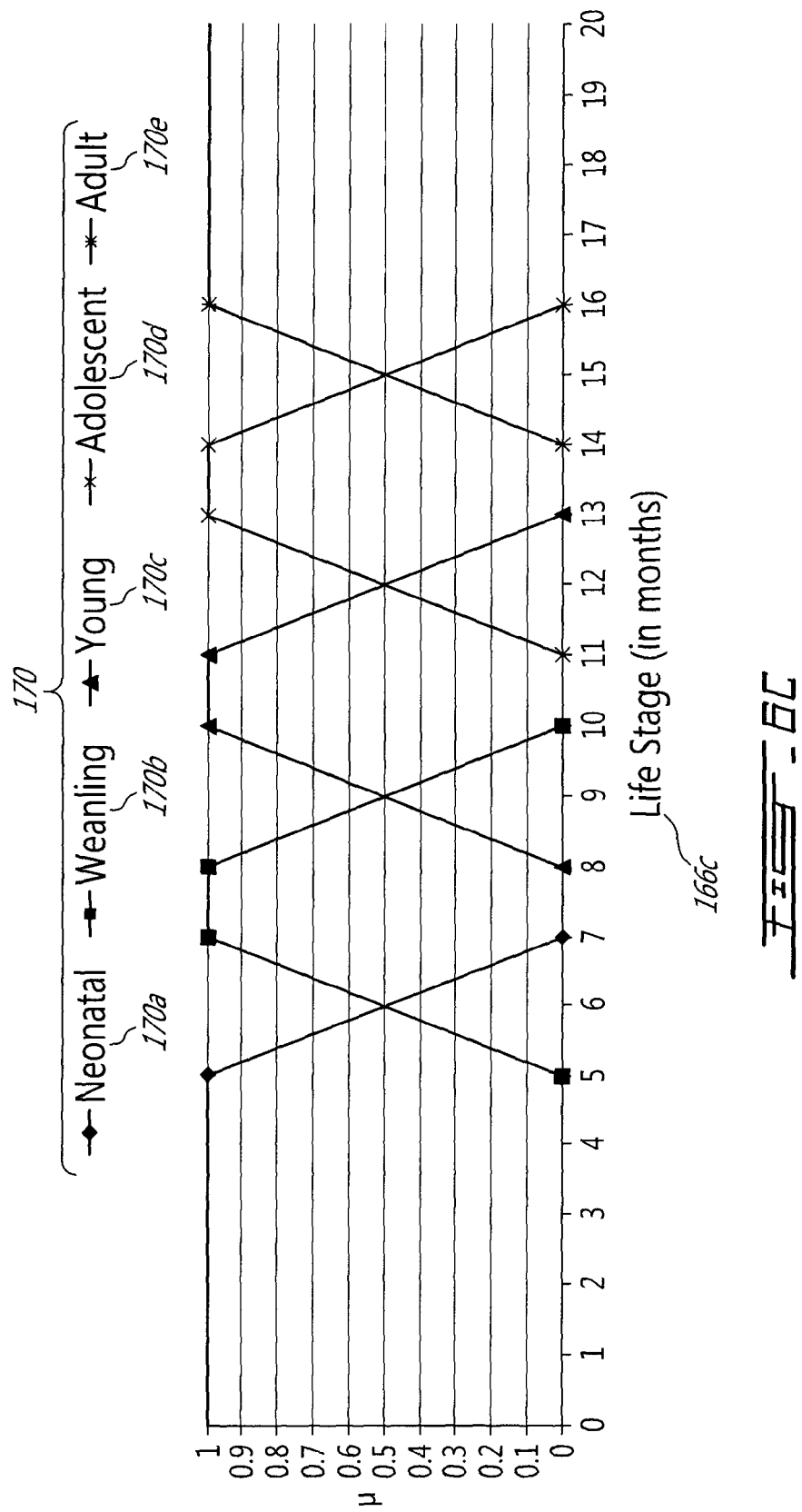
FIG. 6c is a chart of the fuzzy membership function for age in accordance with an illustrative embodiment of the present invention.

Referring now to FIG. 6c, the fuzzy subsets 170 may also overlap, the size, number, and/or degree of overlap depending on the degree of decision control necessary in different regions of scale of measurement. Regions needing finer control may require a larger number of smaller subsets 170. For example and as illustrated in FIG. 6b when referring to a dog, all five "neonatal", "weanling", "young", "adolescent", and "adult" age fuzzy subsets 170a, 170b, 170c, 170d, and 170e overlap. In particular, if the life stages input variable 166c is between 0 and 7 months, this corresponds to the "neonatal" fuzzy subset 170a. If the life stage input variable 166c is between 5 and 10 months, this corresponds to the "weanling" fuzzy subset 170b. If the life stages input variable 166c is between 8 and 13 months, this corresponds to the "young" fuzzy subset 170c. If the life stages input variable 166c is between 11 and 16 months, this corresponds to the "adolescent" fuzzy subset 170d. If the life stages input variable 166c is greater than 14 months, this corresponds to the "adult" fuzzy subset 170e.

Referring now to FIG. 7a, once the input information has been processed, a diagnostic output screen 178 is displayed on the user interface 18. This diagnostic output screen 178 displays important notes about the diagnosis 180, a set of treatment options 182 for the given diagnosis and a further reading section 184 that consists of citations relevant to the information presented above.

Referring now to FIG. 7b, the set of treatment options 182 are further categorized into topical treatment options 186 and systemic treatment options 188.

A treatment 190 is specific to a species and is comprised of the generic name of the medication 190a, the dose 190b, possible routes of administration 190c, the administration interval 190d and the duration of therapy 190e. Additionally, treatments may contain specific notes (reference 196 in FIG. 7c) pertaining to their use for a given disease. These notes are located in the drop down bar which can be accessed by clicking on the treatment or on the "More Info" button 191.

The decision support system 14 may suggest treatments of choice 192 for a specific type of disease or medical problem in a particular animal species. In particular, processing effected by the inference engine (reference 36 in FIG. 3) provides, based on the characteristics of a case entered by a user, a specific action for the user to take. In this manner, specific decision problems are addressed and provided with specific actionable answers. Such treatments of choice 192 are treatments that have been found within the body of literature or within consensus statements by experts in the field to represent the best possible treatment approach for a given disease. All of the treatments of choice 192 contained within this system are referenced and backed by evidence-based medicine. When available, treatments of choice are displayed first in each section and are highlighted.

Combination therapies 194 are composed of two or more individual treatments 190. They are included when evidence has shown that the combination of products is effective for treating a given disease. The combination is indicated by a conjoining bar to illustrate that both individual treatments 190 are required for that therapeutic option.

Referring now to FIG. 7c, pertinent notes 196 may also be presented to provide additional information about a given treatment or medication. The information contained herein is similar to a drug formulary and includes additional treatment notes, contraindications, adverse effects and drug interaction information for that given medication.

Referring now to FIG. 7d in addition to FIG. 7c, if the user identifies a potential issue (e.g. incorrect medication has been suggested) with a specific presented treatment option 190, the user may flag that treatment by selecting the corresponding option 198. The user is then presented with the form 200 depicted in FIG. 7d. In this manner, users can make suggestions to improve the outputs recommended by the decision support system 14. Such treatment options may be stored in the memory 24 for future reference and may only be considered provided an accredited source is specified to validate the user's claim.

Referring back to FIG. 7a, references related to the recommended treatment may further be presented in a Further Reading section 184. The user is therefore made aware of the published guidelines, trade magazines, articles, and the like, which serve to support the set of recommended treatment options 182.

FIGS. 8a to 8h illustrate additional tabs and information to assist with decision making by the practitioner, patient care and client compliance. The more information that the practitioner has at his or her fingertips, the more able they are to make decisions about an ailment. Medical decisions are complex and thus practitioners require a wealth of information to assist with that process; however, they need this information sorted into an organized, retrievable, concise format, which is the reason behind the tab format design. The more able a practitioner is to convey accurate information to their clients, the better the compliance and quality of care will be for the patient.

FIG. 8a is a screen capture of a "Comprehensive Treatment" tab 210 which generates up to three possible options for each species to compliment the primary treatment.

Comprehensive Treatment options include Diet/Lifestyle 210*a*, Supportive Therapy 210*b*, and Adjunct Therapy 210*c*. These options provide treatment recommendations for a given species of dietary modifications, non-pharmaceutical (supportive treatments) and adjunct pharmaceutical therapies which will improve disease outcome.

FIG. 8*b* is a screen shot of a "Disease Highlights" tab 212 which generates up to seven options for each species to provide additional information about the given diagnosis to the practitioner. Disease Highlights options include:
  a. Overview—general information about the disease 212*a*.
  b. Signalment—information about at-risk species and breeds, and age-groups/lifestyles most affected by the disease 212*b*.
  c. History & Presenting Complaint—information about general presenting complaints for a specific diagnosis 212*c*.
  d. Physical Exam Findings—information about what the practitioner should expect on examination of the animal 212*d*.
  e. Diagnostics—tests that should be run and results that should be expected for a given disease 212*e*.
  f. Prevention—how best to prevent the disease 212*f*.
  g. Prognosis—general outcomes associated with the disease 212*g*.

FIG. 8*c* is a screen capture of a "Follow-up/Monitoring" tab 214, which is information to assist practitioners in following up with their patients to optimize patient care and outcomes.

FIG. 8*d* is a screen capture of a "Client Education" tab 216 which is information that should be passed along to the client to optimize communication and compliance in disease treatment.

FIG. 8*e* is a screen capture of a "Latest Research" tab 218 which is information about up and coming therapies or developments in the field that are not yet broadly recommended for general use, but may be important for practitioners to be aware of for future or for outlying cases not responding to conventional therapy.

FIG. 8*f* is a screen capture of an "Associated Diagnoses" tab 220 which provides links to all other associated diagnoses within the system so that the practitioner can quickly reference between diseases without losing their original information.

FIG. 8*g* is a screen capture of the "Prudent Use" tab 222 which provides useful information on the prudent use of antimicrobials in veterinary medicine. This tab is generated and made available on any diagnosis output page that has one or more antibiotic medications prescribed in its treatment options.

FIG. 8*h* is a screen capture of an example of custom tabs 224 that may be displayed for any diagnosis. In this case information relating to ticks is presented, ranging from their preferred habitat and regions to the diseases they may carry, in order to provide users with a better understanding of how the ticks should be treated in a given context.

Referring now to FIG. 9, there is shown a screen capture of an example search performed using the diagnostic search feature 156. This feature allows the user to quickly search the system for a given diagnosis. Search results 270 are presented on the page and the user may then select the desired diagnosis which then presents them with the appropriate treatment output page containing the treatment options associated with that diagnosis.

Referring now to FIG. 10, there is shown a screen capture of a reference library 276 displaying a list of all of the reference sources used by the system. These items are organized by the type of source they represent. Such types include, but are not limited to: journals, textbooks, books, conference proceedings and web sites.

Referring now to FIG. 11, there is shown an administrative user interface that manages the set of diagnoses 280 associated with a given system 282, in this case the Gastrointestinal/Hepatic/Pancreatic system. From here an administrative user may add/remove any of the available systems to/from this list in association with the desired species. Any information which is entered by the administrator, such as the characteristics of the body systems and medications as well as ailments and treatment information, as described below, may be searchable using a search option or icon 284.

Referring now to FIG. 12*a*, there is shown an administrative user interface that manages all diagnoses 286 in the decision support system. From here an administrative user may add/edit a diagnosis and any of its relevant information. The administrative user may also mark a diagnosis as "Not Visible" using the corresponding option 288, to hide the diagnosis from users.

Referring now to FIG. 12*b*, there is shown an administrative user interface 290 that manages all treatment options for a specific diagnosis and species. Any given treatment option may be categorized as topical 292 or systemic 294, as well as being marked as a preferred treatment of choice 296. From here an administrative user may add/edit a treatment and any of its relevant information. Additionally, all diagnostic specific references are managed here (not shown).

Referring now to FIG. 13*a*, there is shown an administrative user interface that manages all medications 300 in the decision support system 14, which includes associated drug classes 302 and trade names 304 for specific medications. From here an administrative user may add/edit a medication and any of its relevant information.

Referring now to FIG. 13*b*, there is shown an administrative user interface for viewing detailed information for a given medication in the decision support system 14. Upon selecting a medication from FIG. 13*a*, the administrator may illustratively be directed to FIG. 13*b*, which presents information, such as adverse effects, contraindications, drug interactions, medication usage criteria and regional approval laws about the selected medication. From here an administrative user may add/edit a medication and any of its relevant information.

User management may be performed from a group standpoint, i.e. users may be managed individually or via groups. Through groups, an administrative user can change permissions and subscriptions for multiple users at once. Administrative users may simply be regular users that belong to one of the administrative groups. These groups may, for example, include the following:
  Super Administrator—Users that belong to this group have full access to all features of the system including: user management and data management.
  Administrator—Users that belong to this group have access to all user management features alone. They do not have permission to manage any of the system's data.
  Data Expert—Users that belong to this group have full access to data management features alone. They do not have permission to manage users or groups.
  Data Reviewer—Users that belong to this group have limited access to data
management. Their access is limited to reviewing data fixes submitted by users of the system. They neither have permission to modify nor manage data, users or groups. Such users have permission to access the decision support system, although its features are limited based on their permission level.

With regards to security, the decision support system may use an adaptive cryptographic hashing function, called BCrypt, based on the Blowfish cipher. It should be understood that any other suitable encryption technique may be used. This method of storing passwords, and other sensitive information, greatly increases the security of the system. The system may use a permissions system to restrict user access to controlled endpoints and system features. Permissions may be manipulated on a user or group basis which allows for both coarse and fine control over which users have access to which features. Subscriptions may also be attributed to groups and/or to users individually. It should be understood that other or additional security features may apply.

While illustrated in the block diagrams as groups of discrete components communicating with each other via distinct data signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment. It should be noted that the present invention can be carried out as a method, can be embodied in a system, and/or on a computer readable medium. The embodiments of the invention described above are intended to be exemplary only. The scope of the invention is therefore intended to be limited solely by the scope of the appended claims.

The invention claimed is:

1. A computer-based decision support system for animals, the system comprising:
  a memory populated with:
    a plurality of diagnoses each associated with at least one of a plurality of species-specific treatment protocols each adapted for treating at least one animal species and at least one ailment; and
    a plurality of rules applicable to the plurality of diagnoses for identifying an appropriate treatment option,
    each one of the plurality of treatment protocols and each one of the plurality of rules supported by evidence-based research;
  a processor; and
  at least one application stored in the memory and comprising an inference engine, the at least one application executable by the processor configured to
    receive input data identifying a first species and representative of a diagnosis of a first ailment for the first species,
    retrieve, by the inference engine, from the memory the at least one treatment protocol associated with the diagnosis and the first species as received,
    select, by the inference engine, at least one rule from the plurality of rules based on the input data and apply, by the inference engine, the at least one rule to the at least one treatment protocol to identify treatment appropriate for treating the first species and the first ailment; and
    output the appropriate treatment as identified.

2. The system of claim 1, wherein the at least one application is executable for receiving medical data comprising at least one of a symptom, an affected body site, and a diagnostic test result, retrieving from the memory the plurality of diagnoses, comparing the received medical data to the plurality of diagnoses for establishing a tentative diagnosis for the animal, and outputting the tentative diagnosis.

3. The system of claim 2, wherein the at least one application is executable for receiving the input data indicative of a validation of the tentative diagnosis.

4. The system of claim 1, wherein the memory is populated with at least one fuzzy rule having at least one instruction associated therewith and further wherein the at least one application is executable for applying fuzzy logic to execute the at least one instruction.

5. The system of claim 1, wherein the at least one application is executable for receiving the input data comprising at least one parameter selected from a group comprising of an age of the animal, a health condition of the animal, and a drug therapy currently prescribed to the animal, and further wherein the memory is populated with at least one exclusion rule applicable for excluding a selected one of the plurality of treatment protocols if the at least one parameter meets a predetermined criterion.

6. The system of claim 5, wherein the at least one application is executable for associating a risk with the selected one of the plurality of treatment protocols if the predetermined criterion is met and for outputting an alert indicative of the risk.

7. The system of claim 1, wherein the memory is populated with therapy information associated with each one of the plurality of treatment protocols, the therapy information comprising at least one of an identification of a drug, a dosage of the drug, a route of administration of the drug, a duration of administration, a frequency of administration, a contraindication of the drug, and an adverse effect of the drug, and further wherein the at least one application is executable for retrieving the therapy information associated with the at least one treatment protocol associated with the diagnosis and outputting the retrieved therapy information.

8. The system of claim 7, wherein the at least one application is executable for establishing on the basis of the retrieved therapy information a ranking of the at least one treatment protocol associated with the diagnosis and for outputting the ranking.

9. A computer-based decision support method for animals, the method comprising executing on a processor program code for:
  receiving input data identifying a first species and representative of a diagnosis of a first ailment for the first species;
  retrieving from a memory, by an inference engine, at least one treatment protocol associated with the diagnosis and the first species as received, the memory populated with a plurality of diagnoses each associated with at least one of a plurality of species-specific treatment protocols each adapted for treating at least one animal species and at least one ailment, each one of the plurality of treatment protocols supported by evidence-based research;
  selecting from the memory, by the inference engine, at least one rule, based on the input data, from a plurality of rules stored in the memory and applicable to the plurality of diagnoses for identifying an appropriate treatment option, each one of the plurality of rules supported by the evidence-based research;

applying, by the inference engine, the at least one rule to the at least one treatment protocol to identify treatment appropriate for treating the first species and the first ailment; and outputting the appropriate treatment as identified.

10. The method of claim 9, further comprising receiving medical data comprising at least one of a symptom, an affected body site, and a diagnostic test result, retrieving from the memory the plurality of diagnoses, comparing the received medical data to the plurality of diagnoses for establishing a tentative diagnosis for the animal, and outputting the tentative diagnosis.

11. The method of claim 10, wherein receiving the input data comprises receiving the input data indicative of a validation of the tentative diagnosis.

12. The method of claim 9, wherein retrieving the at least one treatment protocol associated with the diagnosis comprises applying fuzzy logic to execute at least one instruction associated with the at least one rule.

13. The method of claim 9, wherein receiving the input data comprises receiving at least one parameter selected from a group comprising of an age of the animal, a health condition of the animal, and a drug therapy currently prescribed to the animal, and further wherein applying the at least one rule comprises applying at least one exclusion rule applicable for excluding a selected one of the plurality of treatment protocols if the at least one parameter meets a predetermined criterion.

14. The method of claim 13, further comprising associating a risk with the selected one of the plurality of treatment protocols if the predetermined criterion is met and outputting an alert indicative of the risk.

15. The method of claim 9, further comprising retrieving from the memory therapy information associated with the at least one treatment protocol associated with the diagnosis and outputting the retrieved therapy information, the memory populated with therapy information associated with each one of the plurality of treatment protocols, the therapy information comprising at least one of an identification of a drug, a dosage of the drug, a route of administration of the drug, a duration of administration, a frequency of administration, a contraindication of the drug, and an adverse effect of the drug.

16. The method of claim 15, further comprising establishing on the basis of the retrieved therapy information a ranking of the at least one treatment protocol associated with the diagnosis and outputting the ranking.

17. A non-transitory computer readable medium having stored thereon program code executable by a processor for: animal, the program code executable for:

receiving input data identifying a first species and representative of a diagnosis of a first ailment for the first species;

retrieving from a memory, by an inference engine, at least one treatment protocol associated with the diagnosis and the first species as received, the memory populated with a plurality of diagnoses each associated with at least one of a plurality of species-specific treatment protocols each adapted for treating at least one animal species and at least one ailment, each one of the plurality of treatment protocols supported by evidence-based research;

selecting from the memory, by the inference engine, at least one rule, based on the input data, from a plurality of rules stored in the memory and applicable to the plurality of diagnoses for identifying an appropriate treatment option, each one of the plurality of rules supported by the evidence-based research;

applying, by the inference engine, the at least one rule to the at least one treatment protocol to identify treatment appropriate for treating the first species and the first ailment; and outputting the appropriate treatment as identified.

* * * * *